United States Patent [19]

Amutan et al.

[11] Patent Number: 5,985,570
[45] Date of Patent: Nov. 16, 1999

[54] IDENTIFICATION OF AND CLONING A MOBILE TRANSPOSON FROM ASPERGILLUS

[75] Inventors: Maria Amutan, San Jose; Nigel S. Dunn-Coleman, Los Gatos; Eini M. Nyyssonen, Foster City, all of Calif.

[73] Assignee: Genencor International, Inc., Rochester, N.Y.

[21] Appl. No.: 08/982,232

[22] Filed: Dec. 17, 1997

Related U.S. Application Data

[63] Continuation of application No. 08/703,077, Aug. 26, 1996, abandoned, which is a continuation-in-part of application No. 08/408,413, Mar. 21, 1995, abandoned.

[51] Int. Cl.$^6$ .................................................. C12Q 1/68
[52] U.S. Cl. ......................... 435/6; 435/320.1; 435/473
[58] Field of Search ......................... 435/6, 172.3, 320.1, 435/473

[56] References Cited

U.S. PATENT DOCUMENTS

| | | | |
|---|---|---|---|
| 5,102,797 | 4/1992 | Tucker et al. | 435/172.3 |
| 5,137,829 | 8/1992 | Nag et al. | 435/320.1 |
| 5,316,946 | 5/1994 | Phadnis et al. | 435/320.1 |

FOREIGN PATENT DOCUMENTS

WO 96 29414  9/1996  WIPO ........................... C12N 15/81

OTHER PUBLICATIONS

Amutan, et al., "Identification and cloning of a mobile transposon from *aspergillus niger* var. awamori," Curr. Genet, V. 29, pp. 468–473 (1996).

Bryan et al., "Insertion and Excision of the Transposable element *mariner* in Drosophila", Genetics (1990), 125(1), 103–14 Coden:Gentae; ISSN:0016–6731.

Lidholm, et al., "The transposable element mariner mediates germline transofrmation in Drosophila melanogaster", *Genetics* (1993), 134(3), 859–68 Coden:Gentae; ISSN:0016–6731.

Nyssonan et al., "The Transposable element Tan 1 of Aspergillus niger var. awamori, a new member of the Fot1 family", *Molecular and General Genetics*, V. 253, No. 1–2, Nov. 27, 1996, Berlin DE pp. 50–56, XP002049288, Nov. 27, 1996.

Tenzen et al., "Site–specific transposition of insertion sequence IS630" see abstract,*J. Bacteriol.*, (1990), 172(7), 3830–6 Coden: Jobaay; ISSN: 0021–9193, 1990, XP000576437.

Cambareri et al., *Mol. Gen. Genet.* (1994) 242:658–665.

Cove, D. *Heredity* (1976) 36:191–203.

Daboussi et al., *Genetica* (1994) 93:49–59.

Daboussi et al., *Mol. Gen. Genet.* (1992) 232:12–16.

Dunn–Coleman et al., "Commercial levels of chymosin production by Aspergillus , " Bio/Technology (1991) 9:976–981.

Dunn–Coleman et al., *Mol. Gen. Genet* (1981) 182:234–239.

Gems et al., *Gene* (1991) 98:61–67.

Glayzer et al., *Mol. Gen. Genet* (1995) 249:432–438.

Kachroo et al., *Mol. Gen. Genet.* (1994) 245:339–348.

Kinsey, J., *Proc. Natl. Acad. Sci.* USA (1993) 90:9384–9387.

Kinsey et al., *Proc. Natl. Acad. Sci.* USA (1989) 86:1929–1933.

Lebrum et al., *Fungal Genetics News Letter* (1994) 41A:52.

McHale, et al., *Mol. Gen. Genet.* (1992) 233:337–347.

Minetoki et al., "Nucleotide sequence and expression of alpha–glucosidase–encoding gene (agdA) from *Aspergillus oryzae*, " Biosci. Biotechnol. Biochem. (1995) 59:1516–1521.

Schectman, M., *Mol. Cell. Biol.* (1987) 7:3168–3177.

Walden et al., *Agro–Food–Industry–Hi–Tech*, (1994) Nov./Dec. 9–12.

International Search Report, attached.

*Primary Examiner*—James Ketter
*Attorney, Agent, or Firm*—Margaret A. Horn; Debra J. Glaister

[57] ABSTRACT

There are provided novel transposable elements isolated from Aspergillus. Also provided are novel fragments comprising the inverted repeat(s) of the transposable elements, such fragments being useful as probes to isolate transposable elements from other filamentous fungi.

23 Claims, 13 Drawing Sheets

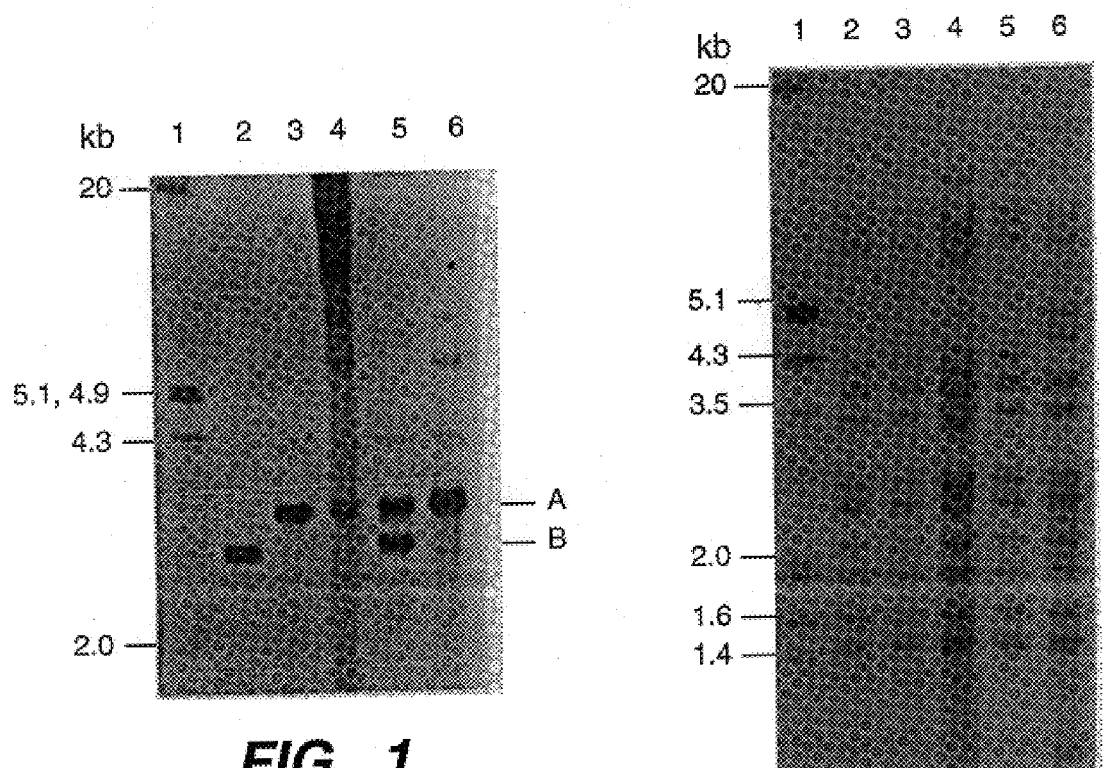
FIG._1
FIG._3
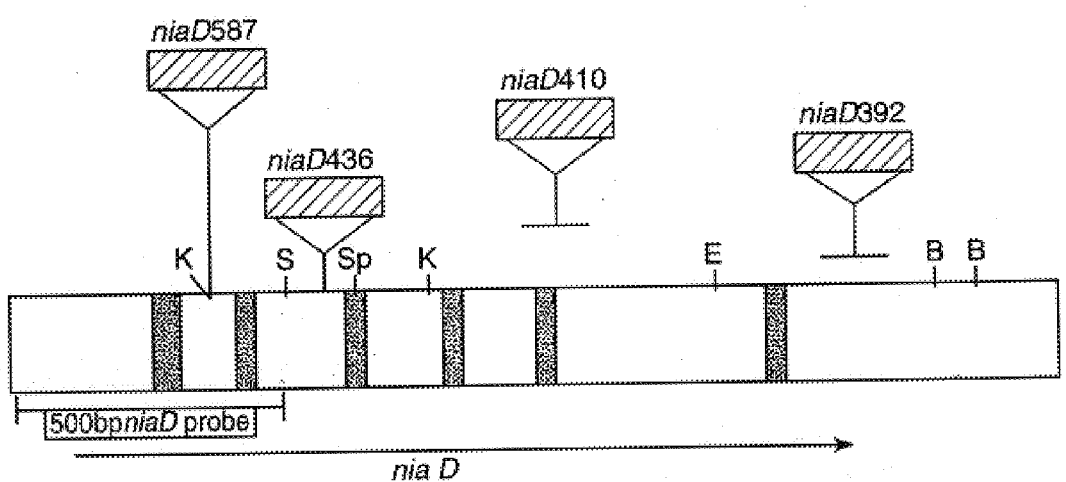
FIG._2

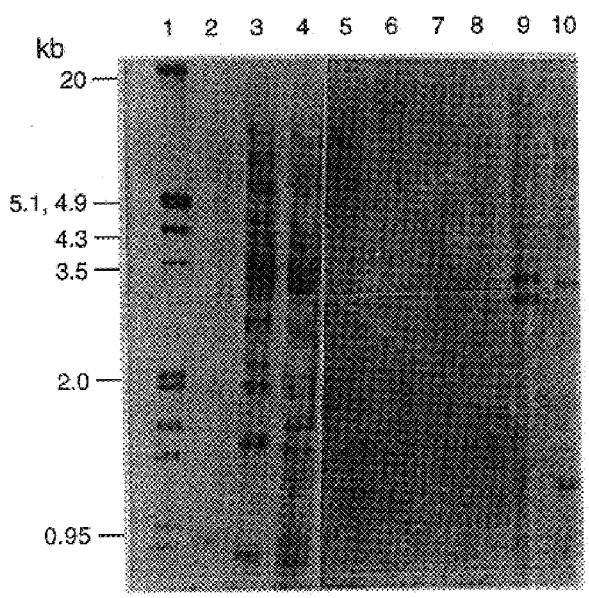
FIG._4
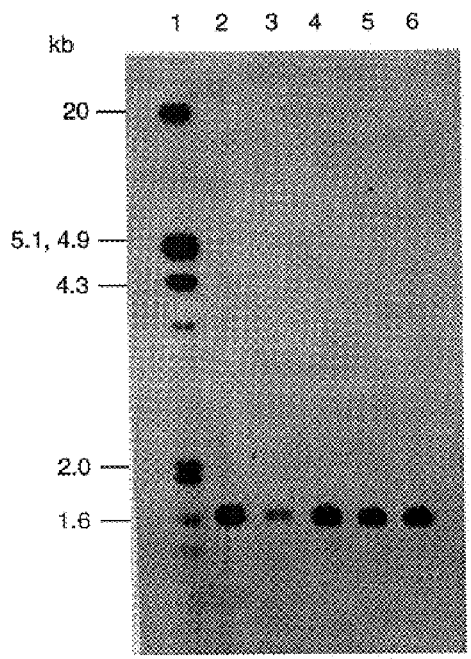
FIG._5

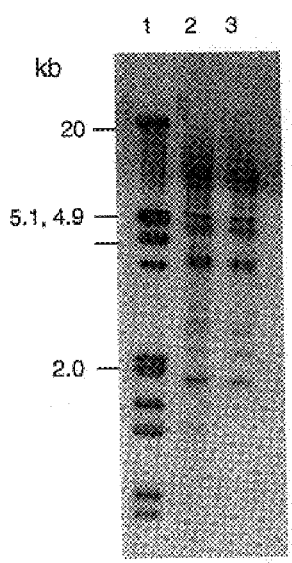 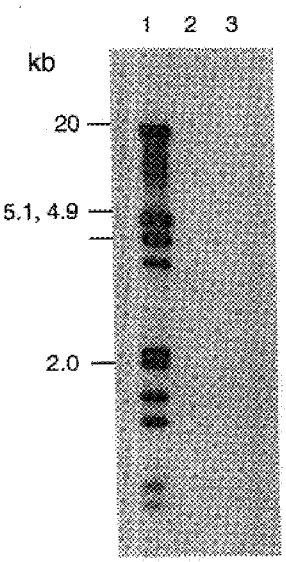 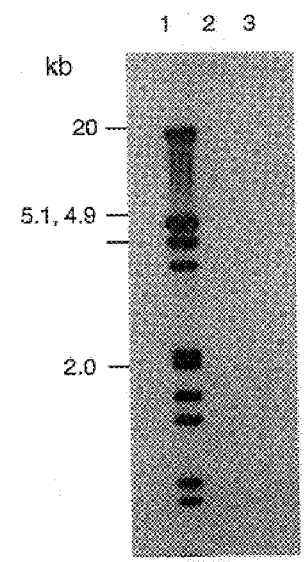
FIG._6A          FIG._6B          FIG._6C tgtcgacggctctctggactggcccaatgatggcagatatcctacggagtgcga agcctttgaggaaagccaagta<u>ACGTAATCAA CGGTCGAACG GGCCACACGG</u>

<u>TCAGGCGGGC CATC</u>CTGAAA TCCCATATAA AAGATGTCTT GGGGATTCTA

TTATATATCA ACCAGTACTA CTTCTATGAA GCTCTAACTT TGTAGATAGT

TATATATATA AGAATAAGTA TTCCATGAAT TTTTCAGATT TTAGAATTTT

TACTTTGATA ATGAAACCAG ATTCTTATAT AAAACATATA AATACAGATA

TTGTAATATG ATAAGTCCAT AAGTAAAAGT ATATTCATTT TTAGAAGGTA

TATAGATATT ATTTATATTA TTTAAAATCT ATATAGAAGA AATCTAATTC

TTCTAGACCT GGATGGTAGA GATATATTAT GTTTAAAAAG ATATCTTTTG

TATAGTATTA CCA<u>GATGGCC CGCCTGACCG TGTGGCCCGT CCGACCGTTG</u>

<u>ATTACGT</u>tatgtctgcatggagggagctgataagctggtaagttaccttatcca tccatgcatgcagtgccctga

FIG._7

```
  1 ACGTAATCAA CGGTCGGACG GGCCACACGG TCAGGCGGGC CATCCCTTCG AAAACACCAC   60
 61 CTTGAATCAC CTACCCGAGG CTTTTCAACC ACCACAAATG CCACCAAAAG CATCTATCCC  120
                                              M  P  P  K  A  S  I  P
121 ATCAAAATCG CAGGTGGAGC AGGAAGGCAG GATTCTTCTT GCCATTGAAG CTATTCAGAA  180
     S  K  S  Q  V  E  Q  E  G  R  I  L  L  A  I  E  A  I  Q  K
181 AGGCCAAATC ACTAGTATTC GTGAAGCAGC GCGTGTTTAT GACGTCGCTC GAACTACTCT  240
     G  Q  I  T  S  I  R  E  A  A  R  V  Y  D  V  A  R  T  T  L
241 CCAGGCTCGA TTATCTGGAC GTGTTTTCGC TAAAAATATG ACCAACGCAC GTCAAAAATT  300
     Q  A  R  L  S  G  R  V  F  A  K  N  M  T  N  A  R  Q  K  L
301 GTCAAATAAT GAAGAGGAAT CGCTTGTTAA ATGGATCCTA TCTCTAGATA AGCGAGGAGC  360
     S  N  N  E  E  E  S  L  V  K  W  I  L  S  L  D  K  R  G  A
361 AAGCCCCCGG CCACTTGATA TCAGAGATAT GGCTAATTTG ATTATCTCTA AACGAGGTTA  420
     S  P  R  P  L  D  I  R  D  M  A  N  L  I  I  S  K  R  G  Y
421 TTCAACTGTT GAACAAGTAG GCATCAACTG GGCTTATAGC TTTGTTAAAC GCCACGAATC  480
     S  T  V  E  Q  V  G  I  N  W  A  Y  S  F  V  K  R  H  E  S
481 CCTACGAACT CGATTTGCTA GACGACTCAA CTATCCAAGA GCTAAAATGG AGGATCCTGA  540
     L  R  T  R  F  A  R  L  N  Y  P  R  A  K  M  E  D  P  E
541 AGTTATAAAA GACTGGTTCC AACGCGTACA GGAAGTTATT CAAGAGTACG GGATCTCATC  600
     V  I  K  D  W  F  Q  R  V  Q  E  V  I  Q  E  Y  G  I  S  S
601 AGATGATATA TACAATTTCG ATGAAACAGG GTTTGCTATG GGAATGATTG CTACATATAA  660
     D  D  I  Y  N  F  D  E  T  G  F  A  M  G  M  I  A  T  Y  K
```

FIG._8A

```
 661  AGTAGTAACT AGTTCCCAGA GGGCAGGTCG GCCGTCCCTA GTTCAACCAG GGAATCGGGA   720
       V  V  T   S  S  Q  R   A  G  R   P  S  L    V  Q  P  G   N  R  E

721  ATGGGTCACT CCAATTGAGT GTATTCGCTC TAATGGAGAG GTTCTACCTT CGACCCTGAT   780
       W  V  T   P  I  E  C   I  R  S   N  G  E    V  L  P  S   T  L  I

781  CTTTAAAGGC AAAACACATC TAAAGGCATG GTATGAAGGT CAATCTATTC CTCCTACCTG   840
       F  K  G   K  T  H  L   K  A  W   Y  E  G    Q  S  I  P   P  T  W

841  GAGATTTGAA GTCAGTGATA ATGGTTGGAC TACTGATAAA ATTGGACTTC GATGGCTTCC   900
       R  F  E   V  S  D  N   G  W  T   T  D  K    I  G  L  R   W  L  P

901  AAAACACTTC ATTCCCTTGA TTAGAGGCAA ATCAGTAGGC AAATATAGCC TCCTAGTCCT   960
       K  H  F   I  P  L  I   R  G  K   S  V  G    K  Y  S  L   L  V  L

961  CGATGGCCAC GGTAGTCATT TGACACCTGA ATTCGACCAA TCCTGTGCTG AAAATGAGGT  1020
       D  G  H   G  S  H  L   T  P  E   F  D  Q    S  C  A  E   N  E  V

1021  TATACCTATT TGTATGCCAG CTCATTCGTC CCATCTACTT CAGCCTCTTG ATGTTGGTTG  1080
       I  P  I   C  M  P  A   H  S  S   H  L  L    Q  P  L  D   V  G  C

1081  TTTTAGTGTG CTTAAACGCA CGTACGGAGG CATGGTTCCC AAGCAGATGC AATACGGCCG  1140
       F  S  V   L  K  R  T   Y  G  G   M  V  P    K  Q  M  Q   Y  G  R

1141  CAATCATATC GACAAGCTTG ACTTCTTAGA GGTCTATCCT AAAGCTCACC AGTGTGCTTT  1200
       N  H  I   D  K  L  D   F  L  E   V  Y  P    K  A  H  Q   C  A  L

1201  ATCAAAGTCG AATATAATCA GTGGTTTTAG AGCAACAGGT CTTGTTCCTC TAGATCCTGA  1260
       S  K  S   N  I  I  S   G  F  R   A  T  G    L  V  P  L   D  P  D
```

*FIG. 8B*

```
1261  TCAAGTGCTT TCTCGACTCC ATATTCGCTT GAAAACACCA CCAACCCCGG ATAGCCAGTC   1320
      Q  V  L    S  R  L  H    I  R  L    K  T  P    P  T  P  D    S  Q  S

1321  AAGTGGCTCA GTGCTTCAAA CACCACATAA TATAAAACAC CTTTTGGAGC ATCCAAAATC   1380
      S  G  S    V  L  Q  T    P  H  N    I  K  H    L  L  E  H    P  K  S

1381  AGTGGAACGC CTACTTCGGA AACGGCAAGC AAGTCCAACT TCACCTACAA ACTCTACACT   1440
      V  E  R    L  L  R  K    R  Q  A    S  P  T    S  P  T  N    S  T  L

1441  ACGTCAGCTT CTCAAAGGGT GTGAACTAGC AATAACAAAC TCAATCATAC TGGCTAAGGA   1500
      R  Q  L    L  K  G  C    E  L  A    I  T  N    S  I  I  L    A  K  E

1501  GAATGCGGAA TTACGTGCTA GCCATGAAAA GCAACTACCA AAGAGGAAGC GTTCAAGGAA   1560
      N  A  E    L  R  A  S    H  E  K    Q  L  P    K  R  K  R    S  R  K

1561  GCAGGTGATC TATACAGAAG GCACTACCGT TGAAGAGGCC CAGAGAGCTA TACAGGAAGT   1620
      Q  V  I    Y  T  E  G    T  T  V    E  E  A    Q  R  A  I    Q  E  V

1621  GGAAGAGGTG CAGAATGATG AAGATATTGA GGTTGAACCC CAATCTCAAT ATACGGAGAC   1680
      E  E  V    Q  N  D  E    D  I  E    V  E  P    Q  S  Q  Y    T  E  T

1681  CCCCTCGCGC GCGCCTCCAC GCTGCAGTAA TTGCTTCAAT ATAGGCCACC GACGTACACA   1740
      P  S  R    A  P  P  R    C  S  N    C  F  N    I  G  H  R    R  T  Q

1741  GTGTTCTAAA CCACCTACTA ATTAGTTAGA TAGCTGTTTT TACAAGCATT TATGTTGATT   1800
      C  S  K    P  P  T  N    *
```

FIG._8C

```
1801 TAGAGGCCTC ATTTGGATCA TATCGGGTAA TCCTACCGGG AGATGGCCCG CCTGACCGTG 1860
1861 TGGCCCGCCC GACCGTTGAT TACGTNNNNN ACGTAATCAA CGGTCGGACG GGCCCCCCGG 1915
1916 TCCGGCGGGC CATCTGGTAA TACTATACCA AAGATATCTT TTTAAACATA ATATATCTCT 1975
1976 ACCATCCAGG TCTAGAGAAA TTAGATTTCT TCTATATAGA TTTTAAATAA TATAAATAAT 2035
2036 ATCTATATAC CTTCTAAAAA TGAATATACT TTTACTTATG GACTTATCAT ATTACAATAT 2095
2096 CTGTATTTAT ATGTATTATA TAAGAATCTG GTTTCATTAT CAAAGTAAAA ATTCTAAAAT 2155
2156 CTGAAAAATT CATGGAATAC TTATTCTTAT ATATATAACT ATCTACAAAG TTAGAGCTTC 2215
2216 ATAGAAGTAG TACTGGTTGA TATATAATAG AATCCCCAAG ACATCTTTTA TATGGGATTT 2275
2276 CAGGATGGCC GCCGACCGTG TGGCCCGTCC GACCGTTGAT TACGT 2320
```

*FIG._8D*

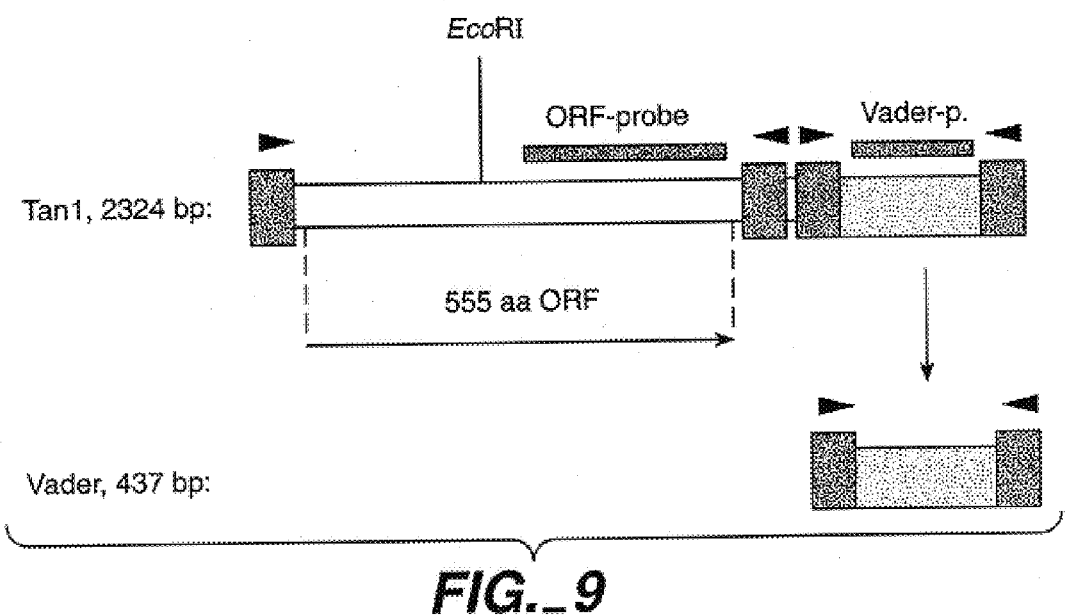
FIG._9
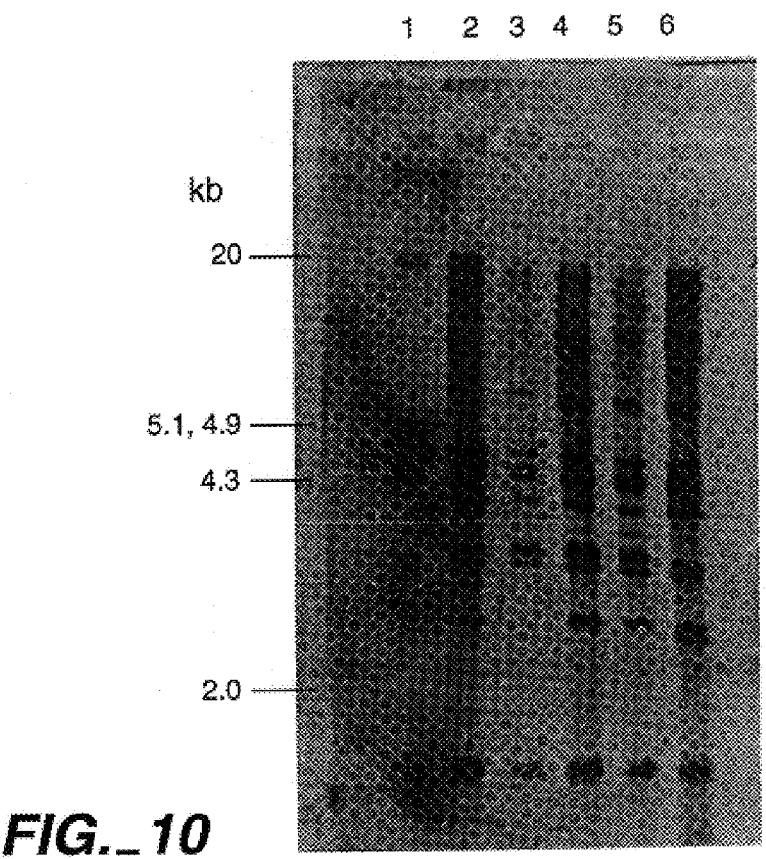
FIG._10

```
  1  ACGTAATCAA CGGTCCGGGCG GGCCACACGG TCAGGCCGGGC CACCCCTTCG AAAACACCAC   60
 61  CTTGAATCAC CTACCCGAGG CTTTTCAACC ACCACAAATG CCACCAAAAG CATCTATCCC  120
                                        M  P  P  K  A  S  I  P
121  ATCAAAATCG CAGGTGGAGC GGGAAGGCAG GATTCTTCTT GCCATTGAAG CTATTGAGAA  180
      S  K  S   Q  V  E  R  E  G  R   I  L  L   A  I  E  A   I  R  K
181  AGGCCAAATC ACTAGTATTC GTGAAGCAGC GCGTGTTTAT GACGTCGCTC GAACTACTCT  240
      G  Q  I   T  S  I  R  E  A  A   R  V  Y   D  V  A  R   T  T  L
241  CCAGGCTCGA TTATCTGGAC GTGTTTTCGC TAAAAATATG ACCAACGCAC GTCAAAAATT  300
      Q  A  R   L  S  G  R  V  F  A   K  N  M   T  N  A  R   Q  K  L
301  GTCAATAAT GAAGAGGAAT CGCTTGTTAA ATGGATCCTA TCTCTAGATA AGCGAGGAGC  360
      S  N  N   E  E  E  S  L  V  K   W  I  L   S  L  D  K   R  G  A
361  AAGCCCCCGG CCACTTGATA TCAGAGATAT GGCTAATTTG ATTATCTCTA AACGAGGTTA  420
      S  P  R   P  L  D  I  R  D  M   A  N  L   I  I  S  K   R  G  Y
421  TTCAACTGTT GAACAAGTAG GCATCAACTG GCTTATAGC TTTGTTAAAC GCCACGAATC  480
      S  T  V   E  Q  V  G  I  N  W   A  Y  S   F  V  K  R   H  E  S
481  CCTACGAACT CGATTGCTA GACGACTCAA CTATCAAAGA GCTAAAATGG AGGATCCTGA  540
      L  R  T   R  F  A  R  R  L  N   Y  Q  R   A  K  M  E   D  P  E
541  AGTTATAAAA GACTGGTTCA AACGCGTACA GGAAGTTATT CAAGAGTACG GGATCTCATC  600
      V  I  K   D  W  F  K  R  V  Q   E  V  I   Q  E  Y  G   I  S  S
601  AGATGATATA TACAATTTCG ATGAAACAGG GTTTGCTATG GGAATGATTG CTACATATAA  660
      D  D  I   Y  N  F  D  E  T  G   F  A  M   G  M  I  A   T  Y  K
```

FIG._11A

```
 661  AGTAGTAACT AGTTCCCAGA GGGCAGGTCG GCCGTCCCTA GTTCAACCAG GGAATCGGGA   720
       V  V  T   S  S  Q  R  A  G  R    P  S  L   V  Q  P  G   N  R  E

721  ATGGGTCACT GCAATTGAGT GTATTCGCTC TAATGGAGAG GTTCTACCTT CGACCCTGAT   780
       W  V  T   A  I  E  C  I  R  S    N  G  E   V  L  P  S   T  L  I

781  CTTTAAAGGC AAAACACATC TAAAGGCATG GTATGAAGGT CAATCTATTC CTCCTACCTG   840
       F  K  G   K  T  H  L  K  A  W    Y  E  G   Q  S  I  P   P  T  W

841  GAGATTTGAA GTCAGTGATA ATGGTTGGAC TACTGATAAA ATTGGACTTC GATGGCTTCA   900
       R  F  E   V  S  D  N  G  W  T    T  D  K   I  G  L  R   W  L  Q

901  AAAACACTTC ATTCCCTTGA TTAGAGGCAA ATCAGTAGGC AAATATAGCC TCCTAGTCCT   960
       K  H  F   I  P  L  I  R  G  K    S  V  G   K  Y  S  L   L  V  L

961  CGATGGCCAC GGTAGTCATT TGACACCTGA ATTCGACCAA CCATCTACTT AAAATGAGGT  1020
       D  G  H   G  S  H  L  T  P  E    F  D  Q   H  L  L     N  E  V

1021  TATACCTATT TGTATGCCTG CTCATTCGTC CAGCCTCTTG ATGTTGGTTG AATACGGCCG  1080
       I  P  I   C  M  P  A  H  S  S    Q  P  L  D  V  G  C   Y  G  R

1081  CTTAAACGCA CGTACGGAGG CATGGTTCAA AAGCAGATGC AAGCAGATGC ATGTTGGTTG  1140
       L  K  R  T  Y  G  G   M  V  Q    K  Q  M  Q  Y  G  R

1141  CAATCATATC GACAAGCTTG ACTTCTTAGA GGTCTATCCT AAAGCTCACC AGTGTGCTTT  1200
       N  H  I   D  K  L  D  F  L  E    V  Y  P   K  A  H  Q   C  A  L

1201  ATCAAAGTCG AATATAATCA GTGGTTTTAG AGCAACAGGT CTTGTCCCTC TAGATCCTGA  1260
       S  K  S   N  I  I  S  G  F  R    A  T  G   L  V  P  L   D  P  D
```

FIG._11B

```
1261  TCAAGTGCTT TCTCGACTCC ATATTCGCTT GAAAACACCA CCAACCCCGG ATAGCCAGTC   1320
       Q  V  L   S  R  L  H   I  R  L    K  T  P    P  T  P  D   S  Q  S

1321  AAGTGGCTCA GTGCTTCAAA CACCACATAA TATAAAACAC CTTTTGAAGC ATCCAAAATC   1380
       S  G  S   V  L  Q  T   P  H  N    I  K  H    L  L  K  H   P  K  S

1381  AGTGGAACGC CTACTTCGGA AACGGCAAGC AAGTCCAACT TCACCTACAA ACTCTACACT   1440
       V  E  R   L  L  R  K   R  Q  A    S  P  T    S  P  T  N   S  T  L

1441  ACGTCAGCTT CTCAAAGGGT GTGAACTAGC AATAACAAAC TCAATCATAC TGGCTAAGGA   1500
       R  Q  L   L  K  G  C   E  L  A    I  T  N    S  I  I  L   A  K  E

1501  GAATGCGGAA TTACGTGCTA GCCATGAAAA AAGAGGAAGC GTTCAAGGAA   1560
       N  A  E   L  R  A  S   H  E  K    K  R  K  R   S  R  K

1561  GCAGGTGATC TATACAGAAG TGAAGAGGCC CAGAGAGCTA TACAGGAAGT   1620
       Q  V  I   Y  T  E  G   E  E  A    Q  R  A  I   Q  E  V

1621  GGAAGAGGTG CAGAATGATG AAGATATTGA GGTTGAACCC CAATCTCAAT ATACGGAGAC   1680
       E  E  V   Q  N  D  E   D  I  E    V  E  P    Q  S  Q  Y   T  E  T

1681  CCCCTCGCGC GCGCCTCCAC GCTGCAGTAA TTGCTTCAAT ATAGGCCACC GACGTACACA   1740
       P  S  R   A  P  P  R   C  S  N    C  F  N    I  G  H  R   T  Q

1741  GTGTTCTAAA CCACCTACTA ATTAGTTAGA TAGCTGTTTT TACAAGCATT TATGTTGATT   1800
       C  S  K   P  P  T  N   *
```

```
1801  TAGAGGCCTC ATTTTGATCA TATCGGGTAA TCCTACCGAG AGATGGCCCG CCTGACCGTG  1860
1861  TGGCCCGCCC GACCGTTGAT TACGT????? ACGTAATCAA CGGTCGGACG GGCCCCCCGG  1915
1916  TCAGGCGGGC CATCTGGTAA TACTATACAA AAGATATCTT TTTAAACATA ATATATCTCT  1975
1976  ACCATCCAGG TCTAGGAGAA TTAGATTTCT TCTATATAGA TTTTAAATAA TATAAATAAT  2035
2036  ATCTATATAC CTTCTAAAAA TGAATATACT TTTACTTATG GACTTATCAT ATTACAATAT  2095
2096  CTGTATTTAT ATGTATTATA TAAGAATCTG GTTTCATTAT CAAAGTAAAA ATTCTAAAAA  2155
2156  TCTGAAAAAT TCATGGAATA CTTATTCTTA TATATATAAA CTATCTACAA AGTTAGAGCT  2215
2216  TCATAGAAGT AGTACTGGTT GATATATAAT AGAATCAAAA AGACATCTTT TATATGGGAT  2275
2276  TTCAGGATGG CCCGCCCTGAC CGTGTGGCCC GTTCGACCGT TGATTACGT              2324
```

5,985,570

SEQUENCE LISTING (1) GENERAL INFORMATION:

(iii) NUMBER OF SEQUENCES: 17

(2) INFORMATION FOR SEQ ID NO: 1:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 1:

```
ACGTAATCAA CGGTCGGGCG GGCCACACGG TCAGGCGGGC CACCC              45
```

(2) INFORMATION FOR SEQ ID NO: 2:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 2:

```
GATGGCCCGC CTGACCGTGT GGCCCGCCCG ACCGTTGATT ACGT               44
```

(2) INFORMATION FOR SEQ ID NO: 3:

(i) SEQUENCE CHARACTERISTICS:
        (A) LENGTH: 437 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 3:

```
ACGTAATCAA CGGTCGAACG GGCCACACGG TCAGGCGGGC CATCCTGAAA TCCCATATAA    60

AAGATGTCTT GGGGATTCTA TTATATATCA ACCAGTACTA CTTCTATGAA GCTCTAACTT   120

TGTAGATAGT TATATATATA AGAATAAGTA TTCCATGAAT TTTTCAGATT TTAGAATTTT   180

TACTTTGATA ATGAAACCAG ATTCTTATAT AAAACATATA AATACAGATA TTGTAATATG   240

ATAAGTCCAT AAGTAAAAGT ATATTCATTT TTAGAAGGTA TATAGATATT ATTTATATTA   300

TTTAAAATCT ATATAGAAGA AATCTAATTC TTCTAGACCT GGATGGTAGA GATATATTAT   360

GTTTAAAAAG ATATCTTTTG TATAGTATTA CCAGATGGCC CGCCTGACCG TGTGGCCCGT   420
```

```
CCGACCGTTG ATTACGT                                                          437

(2) INFORMATION FOR SEQ ID NO: 4:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 4:

ACGTAATCAA CGGTCGAACG GGCCACACGG TCAGGCGGGC CATC                              44

(2) INFORMATION FOR SEQ ID NO: 5:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 5:

GATGGCCCGC CTGACCGTGT GGCCCGTCCG ACCGTTGATT ACGT                              44

(2) INFORMATION FOR SEQ ID NO: 6:

(i) SEQUENCE CHARACTERISTICS:
        (A) LENGTH: 2325 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 6:

ACGTAATCAA CGGTCGGACG GGCCACACGG TCAGGCGGGC CATCCCTTCG AAAACACCAC             60

CTTGAATCAC CTACCCGAGG CTTTTCAACC ACCACAAATG CCACCAAAAG CATCTATCCC            120

ATCAAAATCG CAGGTGGAGC AGGAAGGCAG GATTCTTCTT GCCATTGAAG CTATTCAGAA            180

AGGCCAAATC ACTAGTATTC GTGAAGCAGC GCGTGTTTAT GACGTCGCTC GAACTACTCT            240

CCAGGCTCGA TTATCTGGAC GTGTTTTCGC TAAAAATATG ACCAACGCAC GTCAAAAATT            300

GTCAAATAAT GAAGAGGAAT CGCTTGTTAA ATGGATCCTA TCTCTAGATA AGCGAGGAGC            360

AAGCCCCCGG CCACTTGATA TCAGAGATAT GGCTAATTTG ATTATCTCTA AACGAGGTTA            420

TTCAACTGTT GAACAAGTAG GCATCAACTG GGCTTATAGC TTTGTTAAAC GCCACGAATC            480

CCTACGAACT CGATTTGCTA GACGACTCAA CTATCCAAGA GCTAAAATGG AGGATCCTGA            540

AGTTATAAAA GACTGGTTCC AACGCGTACA GGAAGTTATT CAAGAGTACG GGATCTCATC            600

AGATGATATA TACAATTTCG ATGAAACAGG GTTTGCTATG GGAATGATTG CTACATATAA            660

AGTAGTAACT AGTTCCCAGA GGGCAGGTCG GCCGTCCCTA GTTCAACCAG GGAATCGGGA            720

ATGGGTCACT CCAATTGAGT GTATTCGCTC TAATGGAGAG GTTCTACCTT CGACCCTGAT            780

CTTTAAAGGC AAAACACATC TAAAGGCATG GTATGAAGGT CAATCTATTC CTCCTACCTG            840

GAGATTTGAA GTCAGTGATA ATGGTTGGAC TACTGATAAA ATTGGACTTC GATGGCTTCC            900

AAAACACTTC ATTCCCTTGA TTAGAGGCAA ATCAGTAGGC AAATATAGCC TCCTAGTCCT            960

CGATGGCCAC GGTAGTCATT TGACACCTGA ATTCGACCAA TCCTGTGCTG AAAATGAGGT           1020
```

```
TATACCTATT TGTATGCCAG CTCATTCGTC CCATCTACTT CAGCCTCTTG ATGTTGGTTG      1080

TTTTAGTGTG CTTAAACGCA CGTACGGAGG CATGGTTCCC AAGCAGATGC AATACGGCCG      1140

CAATCATATC GACAAGCTTG ACTTCTTAGA GGTCTATCCT AAAGCTCACC AGTGTGCTTT      1200

ATCAAAGTCG AATATAATCA GTGGTTTTAG AGCAACAGGT CTTGTTCCTC TAGATCCTGA      1260

TCAAGTGCTT TCTCGACTCC ATATTCGCTT GAAAACACCA CCAACCCCGG ATAGCCAGTC      1320

AAGTGGCTCA GTGCTTCAAA CACCACATAA TATAAACAC CTTTTGGAGC ATCCAAAATC       1380

AGTGGAACGC CTACTTCGGA AACGGCAAGC AAGTCCAACT TCACCTACAA ACTCTACACT      1440

ACGTCAGCTT CTCAAAGGGT GTGAACTAGC AATAACAAAC TCAATCATAC TGGCTAAGGA      1500

GAATGCGGAA TTACGTGCTA GCCATGAAAA GCAACTACCA AAGAGGAAGC GTTCAAGGAA      1560

GCAGGTGATC TATACAGAAG GCACTACCGT TGAAGAGGCC CAGAGAGCTA TACAGGAAGT     1620

GGAAGAGGTG CAGAATGATG AAGATATTGA GGTTGAACCC CAATCTCAAT ATACGGAGAC      1680

CCCCTCGCGC GCGCCTCCAC GCTGCAGTAA TTGCTTCAAT ATAGGCCACC GACGTACACA      1740

GTGTTCTAAA CCACCTACTA ATTAGTTAGA TAGCTGTTTT TACAAGCATT TATGTTGATT      1800

TAGAGGCCTC ATTTGGATCA TATCGGGTAA TCCTACCGGG AGATGGCCCG CCTGACCGTG      1860

TGGCCCGCCC GACCGTTGAT TACGTNNNNN ACGTAATCAA CGGTCGGACG GGCCCCCCGG      1920

TCCGGCGGGC CATCTGGTAA TACTATACCA AAGATATCTT TTTAAACATA ATATATCTCT      1980

ACCATCCAGG TCTAGGAGAA TTAGATTTCT TCTATATAGA TTTTAAATAA TATAAATAAT      2040

ATCTATATAC CTTCTAAAAA TGAATATACT TTTACTTATG GACTTATCAT ATTACAATAT      2100

CTGTATTTAT ATGTATTATA TAAGAATCTG GTTTCATTAT CAAAGTAAAA ATTCTAAAAT      2160

CTGAAAAATT CATGGAATAC TTATTCTTAT ATATATAACT ATCTACAAAG TTAGAGCTTC      2220

ATAGAAGTAG TACTGGTTGA TATATAATAG AATCCCCAAG ACATCTTTTA TATGGGATTT      2280

CAGGATGGCC GCCGACCGTG TGGCCCGTCC GACCGTTGAT TACGT                     2325
```

(2) INFORMATION FOR SEQ ID NO: 7:

(i) SEQUENCE CHARACTERISTICS:
        (A) LENGTH: 555 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 7:

```
Met Pro Pro Lys Ala Ser Ile Pro Ser Lys Ser Gln Val Glu Gln Glu
1               5                   10                  15

Gly Arg Ile Leu Leu Ala Ile Glu Ala Ile Gln Lys Gly Gln Ile Thr
        20                  25                  30

Ser Ile Arg Glu Ala Ala Arg Val Tyr Asp Val Ala Arg Thr Thr Leu
    35                  40                  45

Gln Ala Arg Leu Ser Gly Arg Val Phe Ala Lys Asn Met Thr Asn Ala
        50                  55                  60

Arg Gln Lys Leu Ser Asn Asn Glu Glu Glu Ser Leu Val Lys Trp Ile
65                  70                  75                  80

Leu Ser Leu Asp Lys Arg Gly Ala Ser Pro Arg Pro Leu Asp Ile Arg
                85                  90                  95

Asp Met Ala Asn Leu Ile Ile Ser Lys Arg Gly Tyr Ser Thr Val Glu
                    100                 105                 110

Gln Val Gly Ile Asn Trp Ala Tyr Ser Phe Val Lys Arg His Glu Ser
            115                 120                 125
```

-continued

```
Leu Arg Thr Arg Phe Ala Arg Arg Leu Asn Tyr Pro Arg Ala Lys Met
    130                 135                 140
Glu Asp Pro Glu Val Ile Lys Asp Trp Phe Gln Arg Val Gln Glu Val
145                 150                 155                 160
Ile Gln Glu Tyr Gly Ile Ser Ser Asp Asp Ile Tyr Asn Phe Asp Glu
                165                 170                 175
Thr Gly Phe Ala Met Gly Met Ile Ala Thr Tyr Lys Val Val Thr Ser
                180                 185                 190
Ser Gln Arg Ala Gly Arg Pro Ser Leu Val Gln Pro Gly Asn Arg Glu
                195                 200                 205
Trp Val Thr Pro Ile Glu Cys Ile Arg Ser Asn Gly Glu Val Leu Pro
    210                 215                 220
Ser Thr Leu Ile Phe Lys Gly Lys Thr His Leu Lys Ala Trp Tyr Glu
225                 230                 235                 240
Gly Gln Ser Ile Pro Pro Thr Trp Arg Phe Glu Val Ser Asp Asn Gly
                245                 250                 255
Trp Thr Thr Asp Lys Ile Gly Leu Arg Trp Leu Pro Lys His Phe Ile
                260                 265                 270
Pro Leu Ile Arg Gly Lys Ser Val Gly Lys Tyr Ser Leu Leu Val Leu
                275                 280                 285
Asp Gly His Gly Ser His Leu Thr Pro Glu Phe Asp Gln Ser Cys Ala
    290                 295                 300
Glu Asn Glu Val Ile Pro Ile Cys Met Pro Ala His Ser Ser His Leu
305                 310                 315                 320
Leu Gln Pro Leu Asp Val Gly Cys Phe Ser Val Leu Lys Arg Thr Tyr
                325                 330                 335
Gly Gly Met Val Pro Lys Gln Met Gln Tyr Gly Arg Asn His Ile Asp
                340                 345                 350
Lys Leu Asp Phe Leu Glu Val Tyr Pro Lys Ala His Gln Cys Ala Leu
                355                 360                 365
Ser Lys Ser Asn Ile Ile Ser Gly Phe Arg Ala Thr Gly Leu Val Pro
    370                 375                 380
Leu Asp Pro Asp Gln Val Leu Ser Arg Leu His Ile Arg Leu Lys Thr
385                 390                 395                 400
Pro Pro Thr Pro Asp Ser Gln Ser Ser Gly Ser Val Leu Gln Thr Pro
                405                 410                 415
His Asn Ile Lys His Leu Leu Glu His Pro Lys Ser Val Glu Arg Leu
                420                 425                 430
Leu Arg Lys Arg Gln Ala Ser Pro Thr Ser Pro Thr Asn Ser Thr Leu
                435                 440                 445
Arg Gln Leu Leu Lys Gly Cys Glu Leu Ala Ile Thr Asn Ser Ile Ile
    450                 455                 460
Leu Ala Lys Glu Asn Ala Glu Leu Arg Ala Ser His Glu Lys Gln Leu
465                 470                 475                 480
Pro Lys Arg Lys Arg Ser Arg Lys Gln Val Ile Tyr Thr Glu Gly Thr
                485                 490                 495
Thr Val Glu Glu Ala Gln Arg Ala Ile Gln Glu Val Glu Val Gln
                500                 505                 510
Asn Asp Glu Asp Ile Glu Val Glu Pro Gln Ser Gln Tyr Thr Glu Thr
                515                 520                 525
Pro Ser Arg Ala Pro Pro Arg Cys Ser Asn Cys Phe Asn Ile Gly His
    530                 535                 540
Arg Arg Thr Gln Cys Ser Lys Pro Pro Thr Asn
```

(2) INFORMATION FOR SEQ ID NO: 8:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 8:

CCAACCGAGT CCTCAGTATA GAC        23

(2) INFORMATION FOR SEQ ID NO: 9:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 9:

CAACGCTTCA TAGGCGTCCA GATC        24

(2) INFORMATION FOR SEQ ID NO: 10:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 10:

ATATGAATTC ACGTAATCAA CGGTCGGACG GGCCACACGG TCAGGCGGGC CATC        54

(2) INFORMATION FOR SEQ ID NO: 11:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 11:

ATATGAATTC CTTCTTGACT TCCCCGGAAC        30

(2) INFORMATION FOR SEQ ID NO: 12:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 12:

ATATAAGCTT GTCACTGGAC GACATTTCAG        30

(2) INFORMATION FOR SEQ ID NO: 13:

(i) SEQUENCE CHARACTERISTICS:
    (A) LENGTH: 2329 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO: 13:

```
ACGTAATCAA CGGTCGGGCG GGCCACACGG TCAGGCGGGC CACCCCTTCG AAAACACCAC      60

CTTGAATCAC CTACCCGAGG CTTTTCAACC ACCACAAATG CCACCAAAAG CATCTATCCC     120

ATCAAAATCG CAGGTGGAGC GGGAAGGCAG GATTCTTCTT GCCATTGAAG CTATTGAGAA     180

AGGCCAAATC ACTAGTATTC GTGAAGCAGC GCGTGTTTAT GACGTCGCTC GAACTACTCT     240

CCAGGCTCGA TTATCTGGAC GTGTTTTCGC TAAAAATATG ACCAACGCAC GTCAAAAATT     300

GTCAAATAAT GAAGAGGAAT CGCTTGTTAA ATGGATCCTA TCTCTAGATA AGCGAGGAGC     360

AAGCCCCCGG CCACTTGATA TCAGAGATAT GGCTAATTTG ATTATCTCTA AACGAGGTTA     420

TTCAACTGTT GAACAAGTAG GCATCAACTG GCTTATAGC TTTGTTAAAC GCCACGAATC      480

CCTACGAACT CGATTTGCTA GACGACTCAA CTATCAAAGA GCTAAAATGG AGGATCCTGA     540

AGTTATAAAA GACTGGTTCA AACGCGTACA GGAAGTTATT CAAGAGTACG GATCTCATC     600

AGATGATATA TACAATTTCG ATGAAACAGG GTTTGCTATG GAATGATTG CTACATATAA      660

AGTAGTAACT AGTTCCCAGA GGGCAGGTCG GCCGTCCCTA GTTCAACCAG GAATCGGGA     720

ATGGGTCACT GCAATTGAGT GTATTCGCTC TAATGGAGAG GTTCTACCTT CGACCCTGAT     780

CTTTAAAGGC AAAACACATC TAAAGGCATG GTATGAAGGT CAATCTATTC CTCCTACCTG     840

GAGATTTGAA GTCAGTGATA ATGGTTGGAC TACTGATAAA ATTGGACTTC GATGGCTTCA     900

AAAACACTTC ATTCCCTTGA TTAGAGGCAA ATCAGTAGGC AAATATAGCC TCCTAGTCCT     960

CGATGGCCAC GGTAGTCATT TGACACCTGA ATTCGACCAA TCCTGTGCTG AAAATGAGGT    1020

TATACCTATT TGTATGCCTG CTCATTCGTC CCATCTACTT CAGCCTCTTG ATGTTGGTTG    1080

TTTTAGTGTG CTTAAACGCA CGTACGGAGG CATGGTTCAA AAGCAGATGC AATACGGCCG    1140

CAATCATATC GACAAGCTTG ACTTCTTAGA GGTCTATCCT AAAGCTCACC AGTGTGCTTT    1200

ATCAAAGTCG AATATAATCA GTGGTTTTAG AGCAACAGGT CTTGTTCCTC TAGATCCTGA    1260

TCAAGTGCTT TCTCGACTCC ATATTCGCTT GAAAACACCA CCAACCCCGG ATAGCCAGTC    1320

AAGTGGCTCA GTGCTTCAAA CACCACATAA TATAAAACAC CTTTTGAAGC ATCCAAAATC    1380

AGTGGAACGC CTACTTCGGA AACGGCAAGC AAGTCCAACT TCACCTACAA ACTCTACACT    1440

ACGTCAGCTT CTCAAAGGGT GTGAACTAGC AATAACAAAC TCAATCATAC TGGCTAAGGA    1500

GAATGCGGAA TTACGTGCTA GCCATGAAAA GCAACTACCA AAGAGGAAGC GTTCAAGGAA    1560

GCAGGTGATC TATACAGAAG GCACTACCGT TGAAGAGGCC CAGAGAGCTA TACAGGAAGT    1620

GGAAGAGGTG CAGAATGATG AAGATATTGA GGTTGAACCC CAATCTCAAT ATACGGAGAC    1680

CCCCTCGCGC GCGCCTCCAC GCTGCAGTAA TTGCTTCAAT ATAGGCCACC GACGTACACA    1740

GTGTTCTAAA CCACCTACTA ATTAGTTAGA TAGCTGTTTT TACAAGCATT TATGTTGATT    1800

TAGAGGCCTC ATTTTGATCA TATCGGGTAA TCCTACCGAG AGATGGCCCG CCTGACCGTG    1860

TGGCCCGCCC GACCGTTGAT TACGTNNNNN ACGTAATCAA CGGTCGGACG GGCCCCCCGG    1920

TCCGGCGGGC CATCTGGTAA TACTATACAA AAGATATCTT TTTAAACATA ATATATCTCT    1980

ACCATCCAGG TCTAGGAGAA TTAGATTTCT TCTATATAGA TTTTAAATAA TATAAATAAT    2040

ATCTATATAC CTTCTAAAAA TGAATATACT TTTACTTATG GACTTATCAT ATTACAATAT    2100
```

```
CTGTATTTAT ATGTATTATA TAAGAATCTG GTTTCATTAT CAAAGTAAAA ATTCTAAAAA    2160

TCTGAAAAAT TCATGGAATA CTTATTCTTA TATATATAAA CTATCTACAA AGTTAGAGCT    2220

TCATAGAAGT AGTACTGGTT GATATATAAT AGAATCAAAA AGACATCTTT TATATGGGAT    2280

TTCAGGATGG CCCGCCTGAC CGTGTGGCCC GTTCGACCGT TGATTACGT              2329
```

(2) INFORMATION FOR SEQ ID NO: 14:

(i) SEQUENCE CHARACTERISTICS:
      (A) LENGTH: 555 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO: 14:

```
Met Pro Pro Lys Ala Ser Ile Pro Ser Lys Ser Gln Val Glu Arg Glu
1               5                   10                  15

Gly Arg Ile Leu Leu Ala Ile Glu Ala Ile Arg Lys Gly Gln Ile Thr
            20                  25                  30

Ser Ile Arg Glu Ala Ala Arg Val Tyr Asp Val Ala Arg Thr Thr Leu
        35                  40                  45

Gln Ala Arg Leu Ser Gly Arg Val Phe Ala Lys Asn Met Thr Asn Ala
    50                  55                  60

Arg Gln Lys Leu Ser Asn Asn Glu Glu Glu Ser Leu Val Lys Trp Ile
65                  70                  75                  80

Leu Ser Leu Asp Lys Arg Gly Ala Ser Pro Arg Pro Leu Asp Ile Arg
                85                  90                  95

Asp Met Ala Asn Leu Ile Ile Ser Lys Arg Gly Tyr Ser Thr Val Glu
            100                 105                 110

Gln Val Gly Ile Asn Trp Ala Tyr Ser Phe Val Lys Arg His Glu Ser
        115                 120                 125

Leu Arg Thr Arg Phe Ala Arg Arg Leu Asn Tyr Gln Arg Ala Lys Met
    130                 135                 140

Glu Asp Pro Glu Val Ile Lys Asp Trp Phe Lys Arg Val Gln Glu Val
145                 150                 155                 160

Ile Gln Glu Tyr Gly Ile Ser Ser Asp Asp Ile Tyr Asn Phe Asp Glu
                165                 170                 175

Thr Gly Phe Ala Met Gly Met Ile Ala Thr Tyr Lys Val Val Thr Ser
            180                 185                 190

Ser Gln Arg Ala Gly Arg Pro Ser Leu Val Gln Pro Gly Asn Arg Glu
        195                 200                 205

Trp Val Thr Ala Ile Glu Cys Ile Arg Ser Asn Gly Glu Val Leu Pro
    210                 215                 220

Ser Thr Leu Ile Phe Lys Gly Lys Thr His Leu Lys Ala Trp Tyr Glu
225                 230                 235                 240

Gly Gln Ser Ile Pro Pro Thr Trp Arg Phe Glu Val Ser Asp Asn Gly
                245                 250                 255

Trp Thr Thr Asp Lys Ile Gly Leu Arg Trp Leu Gln Lys His Phe Ile
            260                 265                 270

Pro Leu Ile Arg Gly Lys Ser Val Gly Lys Tyr Ser Leu Leu Val Leu
        275                 280                 285

Asp Gly His Gly Ser His Leu Thr Pro Glu Phe Asp Gln Ser Cys Ala
    290                 295                 300

Glu Asn Glu Val Ile Pro Ile Cys Met Pro Ala His Ser Ser His Leu
305                 310                 315                 320
```

```
Leu Gln Pro Leu Asp Val Gly Cys Phe Ser Val Leu Lys Arg Thr Tyr
            325                 330                 335
Gly Gly Met Val Gln Lys Gln Met Gln Tyr Gly Arg Asn His Ile Asp
            340                 345                 350
Lys Leu Asp Phe Leu Glu Val Tyr Pro Lys Ala His Gln Cys Ala Leu
            355                 360                 365
Ser Lys Ser Asn Ile Ile Ser Gly Phe Arg Ala Thr Gly Leu Val Pro
            370                 375             380
Leu Asp Pro Asp Gln Val Leu Ser Arg Leu His Ile Arg Leu Lys Thr
385                 390                 395                 400
Pro Pro Thr Pro Asp Ser Gln Ser Ser Gly Ser Val Leu Gln Thr Pro
                405                 410                 415
His Asn Ile Lys His Leu Leu Lys His Pro Lys Ser Val Glu Arg Leu
                420                 425                 430
Leu Arg Lys Arg Gln Ala Ser Pro Thr Ser Pro Thr Asn Ser Thr Leu
            435                 440                 445
Arg Gln Leu Leu Lys Gly Cys Glu Leu Ala Ile Thr Asn Ser Ile Ile
450                 455                 460
Leu Ala Lys Glu Asn Ala Glu Leu Arg Ala Ser His Glu Lys Gln Leu
465                 470                 475                 480
Pro Lys Arg Lys Arg Ser Arg Lys Gln Val Ile Tyr Thr Glu Gly Thr
                485                 490                 495
Thr Val Glu Glu Ala Gln Arg Ala Ile Gln Glu Val Gly Glu Val Gln
                500                 505                 510
Asn Asp Glu Asp Ile Glu Val Glu Pro Gln Ser Gln Tyr Thr Glu Thr
                515                 520                 525
Pro Ser Arg Ala Pro Pro Arg Cys Ser Asn Cys Phe Asn Ile Gly His
            530                 535                 540
Arg Arg Thr Gln Cys Ser Lys Pro Pro Thr Asn
545                 550                 555

(2) INFORMATION FOR SEQ ID NO: 15:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 15:

ACGTAATCAA CGGTCGGACG GGCCCCCCGG TCAGGCGGGC CATC                    44

(2) INFORMATION FOR SEQ ID NO: 16:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 16:

GGATGGCCCG CCTGACCGTG TGGCCCGTTC GACCGTTGAT TACGT                   45

(2) INFORMATION FOR SEQ ID NO: 17:

(i) SEQUENCE CHARACTERISTICS:
```

-continued (A) LENGTH: 44 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 17:

ACGTAATCGG TAAGCGAGTT GCCCGCGCAA GCGAGTTGCC CACC                44

IDENTIFICATION OF AND CLONING A MOBILE TRANSPOSON FROM ASPERGILLUS

CROSS-REFERENCE TO RELATED APPLICATIONS

This application is a continuation application of U.S. application Ser. No. 08/703,077, filed Aug. 26, 1996, now abandoned, which is a continuation-in-part of U.S. application Ser. No. 08/408,413 filed Mar. 21, 1995, now abandoned, which applications are incorporated herein by reference in their entirety.

FIELD OF THE INVENTION

The present invention is directed at the identification, cloning and sequencing of mobile transposons or transposable elements from *Aspergillus niger* var. *awamori*. The transposable elements, referred to as Vader and Tan 1, are approximately 437 base pair (bp) and 2.3 kb elements, respectively. The Vader and Tan 1 elements are bounded by inverted repeat sequences of 44 and 45 base pairs, respectively. The transposable elements target a "TA" sequence in target DNA during insertion. In addition, the present invention is directed at the identification, cloning and sequencing of one or more transposable element(s) from other filamentous fungi using as a probe DNA comprising the Vader element 44 bp or the Tan 1 element 45 bp inverted repeat isolated from *Aspergillus niger* var. *awamori*. Also provided are methods for utilizing either the Vader or Tan 1 elements to inactivate genes (for example, by inserting the transposon into the gene to be inactivated), to overexpress a gene (by, for example, inserting a known promoter or other regulatory gene within the inverted repeats of Vader or Tan 1 and allowing the DNA of the IR-promoter-IR to jump in front of (and overexpress) a gene of interest) or to act as an activation marker to, for example, identify new promoters.

BACKGROUND OF THE INVENTION

It is well know that transposons are a class of DNA sequences that can move from an episome to a chromosomal site or from one chromosomal site to another. Transposons are known in both prokaryotes, such as bacteria, as well as in eukaryotes, although there have been few transposons isolated from filamentous fungi.

Several groups have looked for transposons in filamentous fungi. The element pogo, which exists in multiple copies and at different sites in different strains of *Neurospora crassa*, was described by Schectman (1) and is believed to be a transposon. To date the most characterized transposon in filamentous fungi is Tad. Tad was isolated as a spontaneous mutant in the am (glutamate dehydrogenase) gene in an Adiopodoume strain of *N. crassa* isolated from the Ivory Coast. To detect mutations caused by insertion of a transposable element, Kinsey and Helber (2) isolated genomic DNA from 33 am mutant strains which were then screened by Southern analysis for restriction fragment size alterations. In two of the mutant strains, the mutation was shown to be caused by the insertion of a 7 kb element (Tad) into the am gene. Subsequently Kinsey (3) demonstrated that Tad was able to transpose between nuclei of heterokaryons, confirming that Tad was a retrotransposon and that there was a cytoplasmic phase involved in the retrotransposition events. More recently, Cambareri et al. (4) demonstrated that Tad was a LINE-like DNA element with two major open reading frames (ORFs) on the plus strand. Typical of LINE-like elements, Tad had no terminal repeats.

Attempts to isolate mobile transposons in laboratory strains of *N. crassa* were unsuccessful.

A second retrotransposon was cloned by McHale et al. (5), who reported the isolation of CfT-1, an LTR-retrotransposon from *Cladosporium fulvum*. This transposon was 6968 bp in length and bounded by identical long terminal repeats of 427 bp, a 5 bp target site duplication. Virus-like particles were detected which co-sediment with reverse transcriptase activity in homogenates of this fungus.

Daboussi et al. (6) were the first to successfully use the niaD (nitrate reductase) gene as a transposon trap. The niaD mutants can be isolated by a direct selection for chlorate resistance (7). The strategy employed was to isolate niaD mutants amongst six isolates belonging to different races of the fungus *Fusarium oxysporum*. More than 100 niaD mutants were isolated from each isolate and examined for instability. One strain, F24, yielded up to 10% unstable niaD mutants. Assuming that the genetic instability of the niaD mutants was caused by transposable elements, it seemed plausible that this isolate contained mobile transposons. A stable niaD mutant in the F24 was transformed with the cloned niaD gene from *A. nidulans* because the *F. oxysporum* niaD gene had not been cloned. Unstable niaD mutants were isolated in transformants containing the *A. nidulans* niaD gene. Two unstable niaD mutants were shown by Southern blot analysis to contain a insertion of 1.9 kb in size. Analysis of this element, Fot1, revealed it was 1928 bp long, had a 44 bp inverted terminal repeats, contained a large open reading frame, and was flanked by a 2 bp (TA) target site duplication. Very recently, Daboussi et al. (8) have reported the cloning of a new transposable element from an unstable niaD mutant. This element, FML (Fusarium mariner-like), is 1280 bp long and has inverted repeats of 27 bp. The FML element inserts into a TA site and excises imprecisely.

Using the characterization of unstable niaD mutants strategy, Lebrun et al. (9) were able to isolate a transposon from *Magnaporthe grisea*. However, in this case the *A. nidulans* niaD gene which was transformed into *M. grisea* by transformation was used as a transposon trap. The element inserted into the niaD gene was shown to belong to a family of *M. grisea* LTR-retrotransposons, Fos 1 (Schull and Hamer, unpublished) and Mag1 (Farman and Leong, unpublished). The cloned retro-element was 5.6 kb and the target site (ATATT) was shown to be duplicated. All revertants from this mutant examined had one copy of the LTR left at the point of insertion. A second transposon, Pot2, from *M. grisea* was recently cloned by Kachroo et al. (10). The strategy used to clone Pot2 was to analyze the fingerprint patterns of repetitive DNA's which were cloned from the *M. grisea* genome. A repetitive family present in both rice and non-rice pathogens of *M. grisea* in high copy number was cloned. The element, 1857 bp in size, has a 43 bp perfect terminal inverted repeats (TIR) and 16 bp direct repeats within the TIRs. An open reading frame was shown to display extensive identity to that of Fot1 of *F. oxysporum*. As with Fot1, the Pot2 element duplicates the dinucleotide TA at the target insertion site. Pot2 was shown to be present at a copy number of approximately 100 per haploid genome.

Several groups have reported looking without success for transposons in laboratory strains of *A. nidulans* (Kinghorn personnel communication, 5). One explanation for the lack of transposons in laboratory strains is that the desirable features of strain stability required for genetic analysis may preclude strains with mobile transposon. By using the niaD gene as a transposon trap we have identified and isolated a transposable element from the industrially important fungus A. niger var. awamori. This element, Vader, is present in approximately 15 copies in A. niger and A. niger var. awamori. Southern analysis of A. nidulans with this element indicates that this transposable element was absent from one laboratory strain and only present as a single copy in a second laboratory strain. These results support the notion that laboratory strains of A. nidulans contain very few transposons.

BRIEF DESCRIPTION OF THE INVENTION

In accordance with the present invention, novel eukaryotic transposable elements from Aspergillus niger var. awamori are provided. The larger transposable element, referred to herein as Tan1, is 2.3 kb in size. The smaller transposable element, referred to herein as Vader, is a 437 bp element (SEQ ID NO:3). Vader is found within the larger element Tan1. The Vader transposable element is a 437 bp element which comprises a 44 bp inverted repeat sequence at either end of the transposable element. Tan1 is approximately a 2325 bp element which comprises 45 bp inverted repeats at either terminus and internal IRs. Tan1 comprises a 555 aa open reading frame (ORF) which codes for a transposase which allows the elements (Tan1 or Vader) to "hop" or insert themselves in the genome of a host. The target for insertion of these novel transposable elements is a "TA" sequence in the target DNA for insertion. The "TA" sequence is repeated at either end of the transposon upon insertion of the transposable element into the target DNA. Therefore, the present invention provides the larger Tan1 transposable element as well as the smaller element (Vader) internal thereto, as well as the DNA encoding each.

Another embodiment of the present invention comprises a fragment of the Vader or Tan1 transposable elements which comprise the 44 or 45 bp (respectively) inverted repeat sequences found at either terminus of the transposable element from A. niger var. awamori, as well as the use of said fragments as probes to hybridize under low stringency conditions to DNA of other filamentous fungi for the isolating and/or cloning of transposable elements from such other filamentous fungi. While the exact 44 bp IR of Vader or the 45 bp IR of Tan1 can be utilized, it is well understood by those skilled in the art that variation of such DNA would also work as a suitable probe. For example, at a minimum, the imperfect direct repeats within the IRs of Tan1 would be suitable to use as probes for isolating transposable elements from other filamentous fungi. Initially the inverted repeat of Vader was used to clone Tan1 using PCR techniques. This work was followed by obtaining a genomic copy of Tan1 from a partial library.

Another embodiment of the present invention is the transposase activity coded for by the ORF of Tan1. This transposase is 555 aa (SEQ ID NOS:7 or 14, PCR and genomic, respectively).

In a process embodiment of the present invention there are provided methods for gene tagging comprising using the transposable elements of the present invention (Vader or Tan1 or any transposable element isolated using the IRs of either) to inactivate genes via insertion of the element into a given gene, thus disrupting or inactivating gene expression. Alternatively, the transposable element can be used in activation tagging (to activate or turn on genes) rather than for gene disruption. For example, by inserting DNA coding a promoter into the transposable element and then allowing such transposable element to become inserted 5' to a desired gene, the promoter may be activated to drive the expression of the desired gene product or to turn on cryptic pathways. Additionally, gene tagging can be utilized to activate marker genes by inserting a marker gene within the IRs of a transposon of the present invention. This marker gene can then "hop" into targeted DNA and, if expression of the marker is selected for, it will be possible to identify the promoter driving such expression. This may lead to identification of isolation of new strong promoters.

BRIEF DESCRIPTION OF THE DRAWINGS

FIG. 1 shows the Southern blot analysis of unstable niaD mutants. PCR-amplified genomic niaD gene from four niaD mutants and UVK143f were digested with BglII (sites are 3' of all inserts). Blot probed with 500 bp fragment of SalI digested PCR product of niaD1 and niaD2. Wild-type band hybridizes at 2.5 kb while gene with insertion hybridizes at 2.9 kb. Lanes: 1=MW marker III (Boehringer Mannheim); 2=UVK143f; 3=niaD410; 4=niaD436; 5=niaD 587; 6=niaD392.

FIG. 2 depicts the mapping of Vader insertions within the niaD gene. The positions of Vader insertions 1–4 (niaD410, niaD436, niaD587 and niaD392, respectively) are shown relative to the six introns of the structural gene coding region. Because the exact site of insertion for Vader-1 and Vader-4 is still unknown, they have been presented using the approximate area of insertion. Relevant restriction sites are shown using the following letters: E=EcoRI, S=SalI, Sp=SphI, K=KpnI, and B=BglII.

FIG. 3 shows Southern blot analysis to determine Vader genomic copy number. Four A. niger var. awamori niaD mutants and UVK143f were digested with EcoRV to completion. EcoRV cuts the Vader sequence once. Hybridization indicates that Vader is present in the genome in more than 14 copies. The hybridizing bands of niaD 392, which are different from the other mutants and UVK143f, suggest that the Vader sequence is mobile. Lanes: 1=MW marker III, 2=UVK143f, 3=niaD410, 4=niaD436, 5=niaD 587, 6=niaD 392.

FIG. 4. Southern blot to determine presence of Vader sequence in other fungi. Other filamentous fungi, an industrial production strain and niaD mutant 392 were digested with EcoRV to completion. Low stringency hybridization (32) indicates that sequences homologous to Vader are present in A. nidulans (FGSC A237), A. cinnamomeus, A. phoenicis, A. foetidus, an industrial A. niger strain. Lanes: 1=MW marker, 2=A. foetidus, 3=an industrial glucoamylase production strain of A. niger (ETC #2663), 4=A. niger var. awamori niaD mutant 392, 5=A. phoenicis (ATCC #11362), 6=A. nidulans (FGSC A691), 7=A. wentii (ATCC #10593), 8=A. versicolor, 9=A. cinnamomeus (ATCC #1027), 10=A. nidulans (FGSC A237).

FIG. 5. Southern blot to determine Tan1 (transposon from A. niger) genomic copy number. Four niaD mutants A. niger var. awamori mutants and UVK143f were digested with EcoRI to completion. EcoRI cuts the Tan1 sequence once. A probe corresponding to the ORF region (see FIG. 9) was used in the hybridization. Hybridization indicates that Tan1 is present as a single copy in the genome. Lanes: 1=MW marker III, 2=UVK143f, 3=niaD410, 4=niaD 436, 5=niaD 587, 6=niaD 392.

FIGS. 6A–6C. Southern blots to determine if the inverted repeats of transposable elements Fot1 and Pot2 will hybridize to elements in A. niger var. awamori . Four niaD mutants A. niger var. awamori mutants were digested with EcoRI to completion. EcoRI cuts the Tan1 sequence once. Inverted repeat oligonucleotide probes of Vader (SEQ ID NO:5), Fot1 and Pot2 were labeled with digoxigenin (Boehringer Mannheim). Lanes: 1=MW marker III, 2=niaD436, 3=niaD587. Blot A (lanes 1–3) and B and C were probed with the labeled inverted repeat probes of Vader, Fot1 and Pot2, respectively.

FIG. 7 shows the sequence of the Vader insertion (SEQ ID NO:3) as generated by PCR. Vader was found to be 437 bp in length. The 44 bp inverted repeat of the Vader insert corresponding to SEQ ID NO:4 (the 5' IR) and SEQ ID NO:5 (the 3' IR), respectively, from the 5' end to the 3' end of Vader are underlined, the single mismatch which occurs in the inverted repeats is identified in bold, and the TA 2 bp duplication is shown in bold print. niaD sequences flanking the element are shown in lower case letters.

FIGS. 8A–8D show the entire DNA sequence of the Tan1 element (SEQ ID NO:6) as generated by PCR, as well as the putative amino acid sequence of the transposase coded for by Tan1 (SEQ ID NO:7). Tan1 as generated by PCR is 2320 bp in length (excluding the unknown nucleotides shown as "N" in the figure) and has a large open reading frame of 1668 bp which encodes for 555 amino acids (SEQ ID NO:7). Tan1 comprises the sequences of four inverted repeats (underlined) similar to those found in Vader.

FIG. 9 shows a schematic presentation of Vader and Tan1 elements. Dark boxes represent the 45 bp (Tan1) and 44 bp (Vader) inverted repeats. The unique EcoRI site in the Tan1 element was used for digestion of genomic DNA in Southern analysis (FIGS. 5 and 10). Bold, horizontal lines above the Tan1 element indicate the probes corresponding to the end of the ORF and Vader used in Southern analysis shown in FIG. 10 and FIG. 5.

FIG. 10 shows Southern analysis of A. niger var. awamori niaD mutants (niaD410, niaD436, niaD587, niaD392) and the wild-type UVK143f: lane 1, molecular weight marker III (Boehringer Mannheim); lane 2, UVK143f; lane 3, niaD410; lane 4, niaD436; lane 5, niaD587; lane 6, niaD392. This blot was probed for the Vader element (see FIG. 9). When this blot (FIG. 10) was superimposed with the blot shown in FIG. 5, one of the illuminated bands from the Vader-probe hybridization overlaid the single band in the ORF-probe hybridization indicating that the Tan1 element is composed of contiguous ORF and Vader elements.

FIGS. 11A–11D show the nucleotide sequence (genomic copy) of Tan1 (SEQ ID NO:13). The amino acid sequence encoding the putative transposase (555 aa) (SEQ ID NO:14) is shown below the DNA sequence in the one-letter amino acid code. The inverted repeats are underlined (SEQ ID NOS:1, 2, 15 and 16, respectively, 5' to 3') and the imperfect direct repeats within the inverted repeats are shown with arrows above or below the sequence. The gaps within the arrows indicate the imperfect nucleotides within the direct repeats. Undetermined sequence is denoted in the figure by question marks and in the sequence listing as "N." The figure shows the DNA sequence as 2324 base pairs, excluding the unknown nucleotides indicated by "?" in the figure.

DETAILED DESCRIPTION OF THE INVENTION

While the specification concludes with claims particularly pointing out and distinctly claiming the subject matter regarded as forming the present invention, it is believed that the invention will be better understood from the following detailed description of preferred embodiments.

Standard biochemical nomenclature is used herein in which the nucleotide bases are designated as adenine (A); thymine (T); guanine (G); and cytosine (C). N connotes any of these nucleotides. As is conventional for convenience in the structural representation of a DNA nucleotide sequence, only one strand is usually shown in which A on one strand connotes T on its complement and G connotes C.

Applicants have isolated two transposable elements from A. niger var. awamori . The cloned element Vader was identified by screening unstable nitrate reductase (niaD) mutants for insertion. This element is present in approximately fifteen copies in the genome of A. niger strains examined. In contrast, the Vader element is present in one copy in only one of the two A. nidulans strains studied. These results explain why several groups have been unsuccessful in isolating active transposons in laboratory A. nidulans strains. A plausible assumption is that "domesticated" strains of A. nidulans have lost their transposons due to repeated manipulation of such strains and the possible discarding of aberrant A. nidulans strains displaying genetic instability.

The Vader element shows similarities to transposable elements cloned from the plant pathogens Pot1 from M. grisea (12) and Fot1 from F. oxysporum (8). The target site for duplication in all three fungi is a 2 bp TA sequence. In the case of Fot1, this transposon does not excise precisely. In two niaD revertants examined, the excision products retained a 4 bp insertion relative to the wild-type gene (TAATTA versus TA). The insertion studied was integrated into an intron, therefore, imprecise excision of Fot1 did not effect the functionality of the niaD gene product. There is no published evidence that Pot2 is a functional element.

A homology search made at the nucleotide level gave a strong 60.7% homology between Tan1 and a 1230 bp overlap to the A. oryzae agdA gene coding for an α-glucosidase (33). This homology search revealed that the last 1.2 kb of a total of 5.2 kb of the α-glucosidase sequence submitted to GenBank is, in fact, part of a novel transposon, hereinafter called Tao1 (transposon Aspergillus oryzae), which also belongs to the Fot1 family. Only the 5' half of the Tao1 element is included in the GenBank sequence, thus, for the lack of comparison, the exact size of the inverted repeat cannot be determined. However, it can be concluded that there are 13 bp perfect direct repeats within the inverted repeat. The inverted repeat is flanked by a TA-dinucleotide, suggesting a commonly occurring TA-insertion site. Direct analyses gave only short ORFs, but when the often-occurring stop codons were ignored, a long ORF was obtained which shared over 50% identity to the Tan1 transposase. Multiple stop codons indicate that the A. oryzae Tao1 is a defective element. This transposable element from A. oryzae, thus, is within the scope of the present invention as, based on the high degree of sequence homology between the Tan1 and Tao1 , it is believed that Tao1 would hybridize to a probe comprising Tan1 or Vader IRs or variations thereof. The sequence of the IR of Tao1 is provided as SEQ ID NO:17. This IR (Tao 1) or the IRs from Tan1 or Vader may be used to isolate other transposable elements from filamentous fungi.

In an attempt to determine if there were transposons similar to those reported for F. oxysporum and M. grisea, synthetic oligomers were made corresponding to the inverted repeats of both Fot1 (7) and Pot2 (10). When Southern analysis of A. niger var. awamori was conducted using the Vader 44 bp inverted repeat (SEQ ID NO:5) as a control, no conclusive hybridizations could be detected with either the Fot1 or Pot2 oligomeric probe. These results indicate that elements with high identity to F. oxysporum Fot1 and M. grisea Pot2 are not found from A. niger var. awamori genome.

With regard to the structure of the Vader element, elements which transpose directly through DNA copies are typified by having inverted terminal repeats. Elements which transpose through reinsertion of the product of reverse transcription of an RNA copy of the element (retroelements) can be without long terminal repeats such as the Drosphilia I element (for a review see (16)). Alternatively, retrotransposons can have long terminal repeats such as the *Drosphilia copia* element. The Vader inverted repeats shown in FIG. 7, SEQ ID NOS:4 and 5, respectively, have a single mismatch. Elements which transpose through DNA copies typically have open reading frame(s) which encode a transposase activity. The Fot1 element is 1.9 kb in length and the Pot1 element 1.8 kb in length. Both the Fot1 and Pot1 elements have ORF encoding for a putative transposase-like protein. The Vader element, although mobile, does not have an ORF and hence it was deduced that the mobility of Vader was dependent upon a transposase activity present elsewhere in the genome. A synthetic 44 bp oligomer of the inverted repeat of Vader (SEQ ID NO:5) was used to clone, via PCR, a 2.3 kb element. This element, called Tan1 (SEQ ID NO:6), comprises four inverted repeats (SEQ ID NOS:1, 2, 15 and 16 from 5' to 3', respectively) similar to those in Vader and has a unique organization IR-ORF-IR-IR-Vader-IR. Tan1 is 2324 bp in length and has a large open reading frame (1668 bp) which encodes a putative transposase comprising 555 amino acids (shown in SEQ ID NOS:7 and 14), which is homologous to Fot1 and Pot2 transposases. Immediately 3' to the second IR (SEQ ID NO:2), which bounds the transposase, is a copy of the Vader element. We hypothesize that at some stage the independent Vader element, although inactive by itself, has arisen from Tan1, resulting in current strains with only one copy of Tan1 providing transposase activity and numerous mobile copies of Vader dispersed in the genome.

Thus, applicants have been the first to identify a transposable element(s) with certain Aspergillus species. These transposable elements are believed to be quite useful in the development of gene tagging systems for Aspergillus or other microorganisms. Basic requirements for developing a gene tagging system are that the tagging element can be distinguished from the endogenous elements, it displays little sequence specificity for transposition and that excision is followed by integration at a new site. More refined tagging systems include ability to monitor excision and reinsertion by, e.g., activation of antibiotic resistance genes and ability to stabilize the mutations by, e.g., a two transposons system (23, 24 and 25).

For development of a tagging system for Aspergillus, it is proposed that the system is tested first in *A. nidulans*, which we have already shown does not have endogenous Tan1 or Vader sequences. However, at this stage the Vader element is altered from the original in such a way that the same construction can be later used in *A. niger* var. *awamori* and be distinguished from the endogenous Vader elements.

In a model tagging system using Vader as the "mutator," a first vector can be constructed for expression of the Vader element, similar to the non-autonomous maize Dc. The internal sequence of the Vader element is altered to contain translation initiation and stop codons in three different frames. This sequence can later be used as a recognition site for a probe in PCR analysis of the mutants. This altered Vader element, Vader-S, is inserted within an expression cassette conferring antibiotic resistance such as hygromycin resistance. Since excision of Vader may not always be precise, Vader-S is inserted in the promoter area (e.g., oliC) between the transcription and translation initiation sites. This disrupted hygromycin phosphotransferase cassette is flanked by marker genes—or alternatively the marker gene upstream of the hygromycin promoter can be placed within Vader. These marker genes can be used for monitoring whether the hygromycin gene, and Vader within it, have integrated in full length. A vector, for example, Vector I, containing these elements will be transferred to *A. nidulans* and transformants expressing the two marker genes, but sensitive to hygromycin, are selected. Screening of mutants at later stages is easier, if the transformant selected for mutagenesis has only one to two copies of Vector I sequences integrated in its genome.

A transformant with only a few (preferentially one) intact Vader-S/hygromycin phosphotransferase cassettes integrated in its genome is retransformed with Vector II, which is an autonomously replicating vector carrying the transposase encoding gene. The autonomously replicating vector, pHELP, used as a basis for DNA construction work, can be segregated away by methods known to those skilled in the art. This enables stabilization of the Vader-S element after the mutagenesis step. Vader-S is activated by a transposase (from Tan1) in pHELP, which can be monitored by activation of the hygromycin resistance gene. Tan1is not cloned into the vector in full length to disrupt its mobility. Again, Vector II contains a marker gene used for screening of transformants and also for monitoring its segregation after the sporulation phase.

Marker genes can either complement host mutations or be dominant markers such as benomyl$^R$, acetamidase or β-glucuronidase (GUS).

In a model system for gene tagging the target gene for mutagenesis should be one with a simple plate screen, e.g., disruption of the niaD gene (by insertion of Vader), which can be screened by selection of chlorate resistant mutants and the gene disruption can be further mapped by a plate test using different nitrogen sources (no growth on nitrate, growth on nitrite, xanthine and uric acid). Another target gene for mutagenesis could be an acid protease gene. It has been shown previously for *A. niger* that disruption of this one protease is sufficient to abolish halo formation almost completely on skim milk plates.

The advantage of using transposon tagging is that the mutants produced can be identified by subsequent isolation of the mutated gene. There are several methods available for PCR amplification of genomic sequences when only one end of the sequence is known—which, in this case, is the transposable element. PCR methods developed for genomic walking are, e.g., "Inverse PCR" (27 and 28), "Vectorette PCR" (29) and "Panhandle PCR" (30).

Setting up the transposon tagging system can be followed by studies of excision frequency, environmental influences on transposition frequency (24, 31), activation of the transposase by a heterologous promoter and effect of altered inverted repeats on transposition.

Transposon tagging does need to be applied for inactivation of genes. Alternatively, tagging can be used to insert promoter sequences in Vader and therein activate genes. A third option is to insert a promoterless marker gene in Vader, in which case the transposon can be used in search for novel, strong fungal promoters.

Experimental

Materials and Methods

Strains. Vader and Tan1 elements were isolated from *Aspergillus niger* var. *awamori* UVK143f, derived from Northern Regional Research Laboratories (NRRL) #3112. *E. coli* JM 101 [F' traD36 lac 1$^q$ Δ(lacZ)M15 proA$^+$B$^+$/supE thi Δ(lac-proAB)] and *Epicurian coli* SURE 2 (Stratagene Cloning Systems, La Jolla, Calif.) were used for propagation of Vader and Tan1 subclones, respectively.

Spontaneous chlorate resistant mutants were derived from *Aspergillus niger* var. *awamori* UVK143f (NRRL #3112). The following Aspergillus strains were obtained from the ATCC: *A. cinnamomeus* (ATCC #1027), *A. wentii* (ATCC #10593), and *A. phoenicis* (ATCC #11362). *A. nidulans* (FGSC #A237), a nitrate reductase structural gene mutant (niaD15), and *A. nidulans* (FGSC #A691), a tryptophan requiring mutant (trpC801), were obtained from Fungal Genetics Stock Center (FGSC), Dept. of Microbiology, University of Kansas Medical Center. *A. versicolor, A. foetidus*, and a proprietary *A. niger* glucoamylase strain are from the Genencor International Inc. culture collection.

Mutant Selection. Spore suspensions ($1 \times 10^8$) of UVK143f were plated on CM agar (11) containing 600 mM $KClO_3$ and 10 mM glutamic acid. Chlorate ($KClO_3$), a toxic analog of nitrate, allows selection of mutants in the nitrate assimilation pathway by chlorate resistance. Plates were incubated at 37° C. until individual colonies of spontaneous mutants could be identified. Single mutants resistant to $KClO_3$ were allowed to sporulate on CM plates and spores from these plates were then streaked onto minimal media (11) with various sole nitrogen sources (10 mM): $NaNO_3$ (nitrate), $NaNO_2$ (nitrite), hypoxanthine, uric acid or $NH_4Cl$ (ammonium chloride). Each of these compounds are intermediate products of the nitrate assimilation pathway. niaD mutants were identified as those resistant to $KClO_3$ and able to grow in the presence of all pathway intermediates, except for $NaNO_3$.

Isolation of Vader via PCR Amplification. Genomic DNA of *A. niger* var. *awamori* niaD mutants and UVK143f was used as template (see Southern Analysis). Primers (50 pmol) used for amplification of the niaD gene were NiaD1(position 142-165 relative to the initiation site of niaD): 5'-CCAACCGAGTCCTCAGTATAGAC-3' (SEQ ID NO:8) and NiaD2 (position 2738-2715): 5'-CAACGCTTCATAGGCGTCCAGATC-3' (SEQ ID NQ:9). Deep Vent (exo⁻) DNA polymerase (New England Biolabs) was used with the buffer and dNTPs provided by the manufacturer. For optimal amplification of the niaD gene the reaction mixture contained 4 mM $MgSO_4$. Denaturation of template DNA, 2 min. at 94° C., was followed by 30 cycles of denaturation (30 sec. at 94° C.), annealing of primers (45 sec. at 55° C.) and extension (4 min. at 72° C.). PCR fragments were purified from gel using the Qiaex DNA gel extraction kit (Qiagen), digested and used for restriction enzyme analysis by standard procedures (12).

Confirmation of Excision Foot Print by PCR Amplification and Sequencing. Template DNA from niaD436 was used in a PCR reaction in an attempt to amplify both the larger niaD sequence with an insert and the shorter niaD fragment resulting from excision of the Vader element. The PCR reaction was conducted as previously described, except for using primers MA003 (positions 359–378): 5'-ATATGAATTCCTTCTTGACTTCCCCGGAAC-3' (SEQ ID NO:11) and NiaD5 (position 1125–1144): 5'-ATATAAGCTTGTCACTGGACGACATTTCAG-3' (SEQ ID NO:12). The gel purified fragment (ca. 800 bp) resulting from the excision event was submitted for sequencing.

Isolation of Tan1 via PCR Amplification. Fungal genomic DNA for PCR and Southern analyses was isolated from mycelia grown in CSL supplemented with 5% fructose (21). Genomic DNA of *A. niger* var. *awamori* niaD 436 mutant (22) was used as a template. A single primer (100 pmol), IR1, was used for amplification of Tan1. The 54-mer IR1 was derived from the 44 bp inverted repeat sequence of Vader preceded by a restriction enzyme recognition site for EcoRI: 5'-ATATGAATTC ACGTAATCAA CGGTCG-GACG GGCCACACGG TCAGGCGGGC CATC-3'(SEQ ID NO:10). Deep Vent (exo⁻) DNA polymerase (New England Biolabs) was used with the buffer and dNTPs provided by the manufacturer. Denaturation of template DNA, 10 min. at 94° C, was followed by 30 cycles of denaturation (1 min. at 94° C.), annealing of primers (1 min. at 55° C.) and extension (6 min. at 72° C.). PCR fragments were purified from agarose gels using the Qiaex DNA gel extraction kit (Qiagen) and subcloned as blunt-ended inserts into EcoRV cut pSL1180 (Pharmacia Biotech).

Estimation of niaD Mutant Reversion Frequency. Spores from niaD mutants niaD392, niaD410, niaD436 and niaD587 were streaked onto minimal media containing $NaNO_3$ as a sole nitrogen source. Nitrate non-utilizing colonies of niaD mutants, which had a spidery appearance and did not sporulate, were streaked onto CM containing 600 mM potassium chlorate ($KClO_3$) and incubated to confluency at 37° C. Ten-fold dilution series of spore suspensions (in 0.8% NaCl-0.25% Tween 80) of niaD392, niaD410, niaD436, niaD587 and UVK143f wild-type spores were plated on minimal media with nitrate (10 mM) to determine reversion frequency, and on CM to determine viability.

Southern Analysis. Genomic DNA for PCR and Southern analysis was isolated (13) from mycelia grown in CSL (13), which contained 600 mM $KClO_3$ in order to reduce reversion of niaD back to the wild-type during cultivation. DNA (10 μg) was digested with either BglII, which leaves the insertion intact in the niaD gene, or with EcoRV, which cuts the insertion element (Vader) once, and thus enables determination of its copy number in the genome. Genomic DNA (approximately 10 pg) of *A. nidulans, A. cinnamomeus, A. versicolor, A. wentii, A. phoenicis, A. foetidus* and of an industrial *A. niger* strain were digested with EcoRV to obtain an estimate of Vader copy number in these fungal genomes. The digested and gel-separated DNA was transferred to a positively-charged nylon membrane (Boehringer Mannheim) by capillary action.

The DNA probe for the niaD gene was derived from the PCR product (UVK143f DNA template amplified with primers NiaD1 (SEQ ID NO:8) and NiaD2 (SEQ ID NO:9)), which was digested with SalI, resulting in a 528 bp probe fragment. The probe for the insertion element, Vader, was derived from a PCR reaction in which niaD436 DNA was used as a template. This PCR product was purified and digested with SalI and SphI and subcloned into the vector pUC19. This subclone was digested with ScaI and XabI to yield a 236 bp fragment which was used for estimation of the copy number of Vader sequences in the genomes of various fungi.

A DNA labeling and detection kit (Genius1, Boehringer Mannheim) was used for random primed labeling of probe DNA with digoxigenin, and for detection with alkaline-phosphatase labeled antibody to digoxigenin.

Hybridization and washing conditions for homologous probes were conducted as recommended by the manufacturer using hybridization buffer without formamide at 68° C (Boehringer Mannheim). Hybridizations for heterologous Southern analysis (i.e., analysis of DNA from other Aspergillus sp.) was conducted using hybridization buffer with 25% formamide at 37° C. Washes were performed as in stringent wash protocol.

Nitrate Reductase Assays. Nitrate reductase assays were performed as described in Dunn-Coleman, et al. (18).

DNA Analysis and Sequence Determination. Sequences were determined using fluorescent-labeled dideoxynucleotide terminators and Taq cycle sequencing on the 373A sequencer (ABI). Commercially available universal and reverse (New England Biolabs) primers were used. Alignment of sequences and prediction of amino acid sequences were performed using DNASTAR (DNASTAR, Inc.). The nucleotide and deduced amino acid sequences were analyzed and compared to those in GenBank, EMBL and Prot-Swiss using Fast A and BLAST programs (Genetics Computer Group, Inc. software package, Madison, Wis.).

Other Probes Used for Southern Analysis. The Tan1 probe was prepared by digesting Tan1 with HindIII and StuI resulting in a 650 bp fragment corresponding to the 3'end of the transposase coding region (ORF-probe in FIG. 9). The Vader element was digested with XabI and ScaI to yield a 236 bp fragment to be used for recognition of internal Vader sequence in Southern analysis (Vader-probe in FIG. 9).

Southern Analysis to Determine Tan1 Copy Number. Aspergillus genomic DNA (10 $\mu$g) was digested with EcoRI, which cuts the Tan1 element once in the transposase coding region and upstream of sequences corresponding to the Vader and Tan1 probes used in hybridizations (FIGS. 5, 9 and 10). DNA labeling and detection kit (Genius 1, Boehringer Mannheim) was used for random primed labeling of probe DNA with digoxigenin and for detection with alkaline-phosphatase labeled antibody to digoxigenin. Hybridization and washing conditions were conducted as recommended by the manufacturer (Boehringer Mannheim).

Isolation of Tan1 from a Partial Genomic Library. It was known from the sequence of the PCR-amplified Tan1 element that Tan1 did not have restriction enzyme recognition sites for BglII and XhoI. A BglII-XhoI digested Southern blot of *Aspergillus niger* var. *awamori* genomic DNA, hybridized with the 650 bp HindIII-StuI Tan1 probe, resulted in identification of a 4.5 kb genomic fragment containing Tan1. *A. niger* var. *awamori* niaD436 DNA was digested with BgII and XhoI and fragments in a size range of 4–5 kb were cloned into pSP73 (Promega). This partial genomic library was screened by colony hybridization using the nonradioactive nucleic acid labeling and detection system from Boehringer Mannheim.

EXAMPLE 1

Isolation of Spontaneous High Frequency Reverting niaD Mutants of *A. niger* var. *awamori*

Assuming that niaD mutants which arise from the insertion of a transposable element would be unstable, a total of 152 niaD mutants, isolated on the basis of spontaneous resistance to chlorate were characterized. To determine if the niaD mutation was unstable, spores from 43 niaD mutants were plated onto medium with nitrate as the sole nitrogen source. Fourteen of the mutants reverted to the wild-type phenotype at a frequency of greater than $1 \times 10^5$. Table 1 summarizes the niaD mutant reversion studies.

TABLE 1

| Mutant | Conidia Plated No. × $10^3$ | No. Wild-Type Colonies | Reversion Frequency × $10^{-4}$ |
| --- | --- | --- | --- |
| niaD392 | 2.9 | 27 | 93 |
| niaD410 | 7.7 | 5 | 6.5 |
| niaD436 | 3.7 | 164 | 443 |
| niaD587 | 18.9 | 12 | 6.3 |

There appeared to be two classes of niaD mutants which reverted at high frequency. The niaD mutants niaD436 and niaD392 reverted at high frequency, while mutants niaD410 and niaD587 yielded smaller numbers of revertant colonies.

The level of nitrate reductase activity was determined using the assay described in (18) from revertant colonies isolated from the niaD 436 mutant. Nitrate reductase activity was detected in 14 of 15 revertants analyzed (see Table 2). A spectrum of activities was detected, suggesting that excision of Vader may not always be precise.

TABLE 2

| Strain | % Nitrate Reductase Activity Compared to Wild-Type |
| --- | --- |
| UVK143f (wild-type) | 100 |
| niaD436 (niaD mutant) | ND[1] |
| Revertants of niaD436: | |
| 1 | 34.7 |
| 2 | 42.8 |
| 3 | 27.7 |
| 4 | 3.5 |
| 5 | ND[1] |
| 6 | 47.4 |
| 7 | 90.4 |
| 8 | 9.8 |
| 9 | 25.4 |
| 10 | 28.9 |
| 11 | 38.2 |
| 12 | 6.9 |
| 13 | 71.7 |
| 14 | 71.7 |
| 15 | 49.7 |

EXAMPLE 2

Cloning of a Vader Element

To determine if an insertion sequence was located within the niaD gene, two primers were synthesized. The first primer, niaD1 (SEQ ID NQ:8), corresponded to position 142-165 of the niaD gene, and niaD2 (SEQ ID NO:9) corresponded to position 2738-2715 of the niaD gene. Genomic DNA was isolated from 14 unstable niaD mutants. This genomic DNA served as a template for the PCR primers. PCR reaction products with 4 niaD mutants (410, 436, 587 and 392) revealed an approximately 440 bp insertion (Vader) in the niaD gene.

For Southern blot analysis, genomic DNA isolated from the wild-type and four niaD mutants (410, 436, 587 and 392) was digested with BglII. The probe used was a SalI digestion fragment of the 500 bp PCR product generated using the niaD1 (SEQ ID NO:8) and niaD2 (SEQ ID NO:9) oligomeric probes. The probe hybridized to a 2.5 kb fragment with wild-type DNA (lane 5, FIG. 1). In the case of the niaD mutants 410 (lane 1, FIG. 1), 436(lane 3, FIG. 1) and 392 (lane 4, FIG. 1), the probe hybridized to a 2.9 kb fragment. These results indicate that these three niaD mutants contain an approximately 440 bp insertion. Interestingly, with the mutant niaD587, the probe hybridized to both a 2.5 kb and 2.9 kb fragment, although mycelium had been grown in the experiment in the presence of KCIO$_3$ to favor growth of the niaD mutant and not revertant cells, the detection of two

[1]Activity non-detectable hybridizable sequences indicated that in some cells Vader had been excised from the niaD gene.

The approximate location of the insertion was determined in each of the four unstable niaD mutants by restriction mapping analysis. The location of the insertion in each of the four mutants examined is shown in FIG. 2. All four mutants had an approximately 440 bp insertion located at different sites within the niaD gene.

EXAMPLE 3

Determination of Vader Copy Number

To determine the Vader copy number a 236 bp ScaI-XabI internal fragment of Vader-2 (cloned from the mutant niaD436) was hybridized to EcoRV cleaved genomic DNA. There is only one EcoRV site within the Vader transposon. Southern blot analysis indicated that there are approximately fifteen copies of Vader sequences in the genome of *A. niger* var. *awamori* . (FIG. 4). The Vader sequences were integrated at identical genomic locations in the three niaD mutants, 410, 436 and 587. However, in the niaD392 mutant, Vader sequences were located in five different locations compared to the three niaD mutants examined. This result was somewhat surprising considering that all four niaD mutants were isolated from the same strain, but provides good evidence for the high mobility of the Vader element in this strain. When a propriety *A. niger* glucoamylase production strain (ETC #2663) was also examined, approximately 15 hybridization signals could be detected. Although some of the hybridization patterns appeared to be identical, clear differences could be seen between *A. niger* var. *awamori* and *A. niger*.

EXAMPLE 4

Isolation of Vader in Other Fungal Species

In an attempt to determine if this transposable element was found in other filamentous fungi, genomic Southern blot analysis was performed using the 236 bp fragment (XabI-ScaI) of Vader sequence as per-Example 3, as a probe (FIG. 5). Two strains of *A. nidulans* were obtained from Fungal Genetics Stock Center (FGSC), FGSC#A691, a nitrate reductase structural gene mutant (niaD15), and FGSC #A237, a tryptophan-requiring mutant (trpC801). No hybridization signals could be visualized with strain A691, and a single strong hybridization signal could be detected with strain A237. These results support the notion that the lack of success in cloning transposable elements from laboratory strains of *A. nidulans* is due to low copy number or absence. Similarly, only one hybridization signal could be detected in *A. foetidus* and *A. phoenicis* , while two hybridization signals were detected in *A. cinnamomeus* . No hybridizations could be detected in *A. wentii* and *A. versicolor*. In addition, no hybridization signals could be detected with *Humicola grisea* var. *thermoidea, Neurospora crassa* and *Trichoderma reesei* (results not shown). These results indicate that the Vader element is most commonly found in *A. niger* var. *awamori* and *A. niger*.

EXAMPLE 5

Excision of the Vader Element

Part of the niaD gene from niaD436 containing the Vader element was amplified using PCR. The PCR amplification resulted in the expected 1200 bp fragment of the Vader element flanked by niaD sequences and a shorter 800 bp fragment resulting from the excision event. Sequencing of the shorter fragment indicated that the Vader element had excised precisely. However, when several revertants of niaD436 and niaD410 were assayed for their nitrate reductase activity (18), a spectrum of activities was detected, suggesting that excision of the Vader element may not always be precise (results not shown).

EXAMPLE 6

Isolation of Tan1

The previously isolated Vader element, although mobile, did not have an ORF encoding transposase activity presumed to be required for excision (22). This observation led to a search for a transposase-encoding larger element, thus an oligomer corresponding to the Vader inverted repeat was synthesized and used for PCR amplification of the genomic *A. niger* var. *awamori* DNA. The PCR amplification resulted in the generation of three DNA fragments: the 0.4 kb Vader element, as expected, and fragments of 1.9 kb and 2.3 kb in length.

Both of the larger PCR-generated fragments were sequenced and the sequences were identical with an exception that the 2.3 kb fragment had an additional 400 bp at the 3'end. Surprisingly this additional sequence at the 3' end was a Vader element, which differed only by a few nucleotides from the previously isolated Vader. The 5' end sequence, shared by both of the 1.9 kb and 2.3 kb fragments, had a single ORF (1668 bp) coding for a protein of 555 amino acids flanked by inverted repeats (IRs). Thus, the 1.9 kb fragment, devoid of the Vader element, had an organization of IR-ORF-IR. The larger 2.3 kb fragment had a unique organization, IR-ORF-IR-IR-Vader-IR, with a total of four inverted repeats (FIGS. 9 and 11). In this larger element the two central inverted repeats, side by side, potentially form a tight hairpin structure, and despite many sequencing attempts with varying conditions, we were unable to determine the sequence between the two inverted repeats. However, the overall length of the PCR product, as determined by electrophoresis, corresponded to the size of the sequence shown in FIG. 11, suggesting that the two central contiguous IRs are not separated by a large segment of DNA.

Due to the organization of the 1.9 kb and 2.3 kb fragments, it was believed that the 1.9 kb fragment could have arisen in PCR from a partial amplification of the 2.3 kb fragment if the 3' IR-primer had annealed to the first central IR instead of the IR in the end of the Vader element. Southern analysis was conducted in order to determine if the 1.9 kb element existed in the genome without the associated Vader element, or whether it was a PCR-artifact derived from a partial amplification of the 2.3 kb element. The two probes used in Southern analysis corresponded to the internal sequence of Vader and to the carboxyterminal part of the ORF (FIG. 9). The genomic DNA from *A. niger* var. *awamori* niaD mutants and UVK1 43f were digested with EcoRI, which cuts once in the coding region of the ORF upstream from the ORF-probe and does not cut Vader. The Southern analysis showed numerous bands for the Vader element (FIG. 10), similar to previous Southern analyses (22). However, only one fragment lit up with the probe corresponding to the ORF and a fragment of the same size (1.6 kb) was recognized by the Vader probe (FIG. 10). It was concluded that the actual element in the genome was the 2.3 kb fragment and that the shorter 1.9 kb had only been a PCR-artifact. The isolated 2.3 kb fragment was designated as Tan1.

A genomic clone of the Tan1 element (2.3 kb) was isolated from a partial genomic library. Restriction enzymes, which were shown not to have any recognition sites in the PCR-amplified Tan1, were used separately and in combinations in Southern analysis of the genomic DNA. A double digestion with BglII and XhoI resulted in a relatively short, 4.5 kb, fragment which hybridized with the ORF-specific probe (data not shown). Genomic DNA fragments cleaved by BglII and XhoI and between 4 kb and 5 kb in size were cloned into pSP73 (Promega). The correct clone containing the Tan1 element was isolated by colony hybridization using the ORF-specific probe. Differences between the sequences of the genomic clone and the PCR-generated Tan1 were minor, even for the flanking IRs which were almost identical even though in the PCR-generated Tan1 the IRs were derived from the Vader IRs (PCR primers). It was seen from the genomic clone of Tan1 that immediately outside of the terminal IRs there were TA-dinucleotides, suggesting a TA target site and its duplication upon insertion. Sequence of the Tan1 genomic clone is shown in FIGS. 11A and 11B [SEQ ID NO:13 (DNA) and SEQ ID NO:14 (amino acid)].

EXAMPLE 7

Insertional Inactivation/Gene Tagging

Vader was cloned by insertional inactivation of the target gene niaD, which encodes nitrate reductase. The target sequence for integration of Vader is TA, a sequence which must be very common in the genome of fungi. Nitrate reductase mutants cannot grow on nitrate and inconsequence are resistant to the toxic analog of nitrate, $KCIO_3$.

It is possible that one of the reasons heterologous protein production in fungi is lower than that of homologously produced protein using the same promoter is that the heterologous protein is being degraded by the cell. If there are genes whose products are responsible for degrading/sequestering foreign protein, it would be advantageous to inactivate those genes. In order to achieve this, a strain is constructed using gene disruption, which lacks the Tan1 gene. Such strain is then used to transform and express a heterologous protein such as the mammalian chymosin protein. It would be advantageous if the activity of such genes could be visualized or selected for on petri dishes. For example chymosin produced in A. niger results in a halo of clearing around a colony grown on skim milk. (See U.S. Pat. No. 5,364,770, the disclosure of which is incorporated herein by reference.)

Having transformed the strain with a construct comprising the desired heterologous protein or polypeptide, one would transform the strain a second time with Vader and Tan1 appropriately modified for gene tagging purposes.

The transformants are then plated on medium which can be used to visualize heterologous protein production, such as skim milk plates in the case of chymosin.

The plates are then screened for increased halo size, which is the result of inactivation of a gene whose product limits foreign protein production.

The inactivated gene can be cloned using the transposon sequences as a marker for cloning strategies. (See generally (19).)

EXAMPLE 8

Elevation of Gene Expression Using Transposons

A reason that heterologous protein production is lower than expected in fungi is presumed to be that genes essential for foreign (heterologous) gene production are NOT expressed at sufficiently high levels in the fungi.

In order to overcome this problem, utilizing the transposable element(s) of the present invention, a strain is constructed in which the native Tan1 gene is inactivated by gene disruption.

This strain is used to express a heterologous protein whose expression can be easily visualized, such as chymosin (U.S. Pat. No. 5,364,770). A second transformation is made with Vader and Tan1, appropriately modified for gene tagging purposes. The internal sequence of Vader is replaced by a promoter sequence. One of the many integration events possible will be the integration of this promoter carrying Vader element into 5' to a gene beneficial to heterologous protein (e.g., chymosin) expression or secretion. Upon insertion, this beneficial gene is activated and such integrant colonies can be screened for, e.g., increased halo size (chymosin). The activated gene can be cloned using the transposon sequences as a marker for cloning strategies.

References

1. Schectman, M. G. (1987) *Mol. Cell. Biol.* 7: 3168–3177
2. Kinsey, J. A. & Hebler, J. (1989) *Proc. Natl. Acad. Sci. USA* 86: 1929–1933
3. Kinsey, J. A. (1993) *Proc. Natl. Acad. Sci. USA* 90: 9384–9387
4. Cambareri, E. B., Helber, J. & Kinsey, J. A. (1994) *Mol. Gen. Genet.* 242: 658–665
5. McHale, M. T., Roberts, I. N., Noble, S. M., Beaumont, C., Whitehead, M. P., Seth, D. & Oliver, R. P. (1992) *Mol. Gen. Genet.* 233: 337–347
6. Daboussi, M. J., Langin, T. & Brygoo, Y. (1992) *Mol. Gen. Genet.* 232: 12–16
7. Cove, D. J. (1976) *Heredity* 36: 191–203
8. Daboussi, M. J. & Langin, T. (1994) *Genetica* 93: 49–59
9. Lebrum, M.-H. Chumley, F. & Valent, B. (1994) *Fungal Genetics News Letter* 41A: 52
10. Kachroo, P., Leong, S. A. & Chattoo, B. B. (1994) *Mol. Gen. Genet.* 245: 339–348
11. Rowlands, R. T. & Turner, G. (1973) *Mol. Gen. Genet.* 126: 201–216
12. Sambrook, J., Fritsch, E. F. & Maniatis, T. (1989) *Molecular Cloning: A Laboratory Manual,* Cold Spring Harbor Laboratory Press, Plainview, N.Y., pp. 1.11–1.85
13. Timberlake, W. E. & Barnard, E. C. (1981) *Cell* 26: 29–37
14. Yanisch-Peron, C., Vieira, J. & Messing, J. (1985) *Gene* 33: 103–119
15. Meseselson, M. & Yuan, R. (1968) *Nature* 217: 1110–1114
16. Charlesworth, B., Snlegowski, P. & Stephan, W. (1994) *Nature* 371: 215–220.
17. Fedoroff, N, V., Furtek, D. B. & Nelson, O. E. (1984) *Proc. Natl Acad. Sci. USA* 81: 3829–3835
18. Dunn-Coleman, N. S., Tomsch, A. D. & Garrett, R. H. (1981) *Molec. Gen. Getet.* 182: 234–239
19. Walden, R. & Schell, J. (1994) *Agro-Food-Industry-Hi-Tech,* Nov/Dec: 9–12
20. Gems, D. H., Johnstone, I. L. & Clutterbuck, A. J. (1991) *Gene* 98: 61–67
21. Dunn-Coleman, N. S., Bloebaum P., Berka, R. M., Bodie, E., Robinson, N., Kodama, K. H., Baliu, E. F., Bower, B., Lamsa, M. & Heinsohn, H. (1991) "Commercial levels of chymosin production by Aspergillus," *Bio/Technology* 9: 976–981
22. Amutan, M., Nyyssonen, E., Stubbs, J., Diaz-Torres, M. R. & Dunn-Coleman, N. (1996) "Identification and cloning of a mobile transposon from *Aspergillus niger* var. *awamori*,"*Curr. Genet.* 29: 468–473
23. Bancroft, I., Bhatt, A., Sjodin, C., Scofield, S., Jones, J. & Dean, C. (1992) *Mol. Gen. Genet* 233: 449–461
24. Bancroft, I. & Dean, C. (1993) *Mol. Gen. Genet.* 240: 65–67
25. Long, D., Martin, M., Sundberg, E., Swinburne, J., Puangsomlee, P. & Coapland, G. (1993) *Proc. Natl. Acad. Sci.* 90: 10370–10374
26. Berka et al. (1990) *Gene* 86: 153–162
27. Ochman, H., Gerber, A. S. & Hart, D. L. (1988) *Genetics* 120: 621–623
28. Williams, J. F. (1989) *Biotechniques* 7: 762–769
29. Arnold, C. & Hodgson, I. J. (1991) *PCR Methods Appl.* 1: 39–42
30. Jones, D. H. & Winistorfer, S. C. (1993) *PCR Methods Appl.* 2: 197–203
31. Brujin, F. J. & Lupski, J. R. (1984) *Gene* 27: 131–149
32. Brown, T. *Current Protocols in Molecular Biology,* Supplements 21, 24, 26 and 29
33. Minetoki, T., Gomi, K., Kitamoto, K., Kumagai, C., Tamura, G. (1995) "Nucleotide sequence and expression of alpha-glucosidase-encoding gene (agdA) from *aspergillus oryzae*," *Biosci. Biotechnol. Biochem.* 59: 1516–1521

We claim:

1. A transposable element isolated from *Aspergillus niger* var. *awamori* comprising a DNA fragment of about 2.3 kb.

2. The transposable element of claim 1 comprising the DNA sequence of SEQ ID NO: 13 or SEQ ID NO:6.

3. A fragment of the transposable element of claim 1 comprising part or all of the DNA sequence selected from the group consisting of SEQ ID NOS:1, 2, 15 and 16.

4. An isolated transposase coded for by the transposable element of claim 1.

5. The transposase of claim 4 comprising the amino acid sequence of SEQ ID NO:14 or SEQ ID NO:7.

6. A transposable element isolated from *Aspergillus niger* var. *awamori* comprising a DNA fragment of approximately 437 base pairs.

7. The transposable element of claim 6 comprising the DNA sequence of SEQ ID NO:3.

8. A fragment of the transposable element of claim 6 comprising part or all of the DNA sequence of SEQ ID NOS:4 or 5.

9. A method of isolating a transposable element from a filamentous fungus, comprising the steps of:
   a) hybridizing fungal DNA under low stringency conditions to a probe, wherein the probe comprises part or all of one of the DNA fragments of claim 3; and
   b) isolating fungal DNA which hybridizes to said probe.

10. The method of claim 9 wherein the probe comprises an imperfect direct repeat within the DNA sequence selected from the group consisting of SEQ ID NOS:1 and 16.

11. A method of isolating a transposable element from a filamentous fungus, comprising the steps of
    a) hybridizing fungal DNA under low stringency conditions to a probe, wherein the probe comprises part or all of one of the DNA fragments of claim 8; and
    b) isolating fungal DNA which hybridizes to said probe.

12. A method of isolating a transposable element from an Aspergillus genomic library, the method comprising probing said library with nucleic acid encoding part or all of the 555 amino acid open reading frame of Tan1 and isolating DNA which hybridizes to said nucleic acid.

13. A method of isolating a transposable element from a filamentous fungus, the method comprising
    a) subjecting fungal DNA to polymerase chain reaction amplification using part or all of one of the DNA fragments of claim 3 or 8 as a primer, thereby generating amplified DNA sequences;
    b) isolating the amplified DNA sequences; and
    c) optionally identifying said amplified DNA sequence.

14. A transposable element isolated by the method of claim 9.

15. A transposable element isolated by the method of claim 11.

16. A transposable element isolated by the method of claim 12.

17. A transposable element isolated by the method of claim 13.

18. A method of isolating activation sequences, comprising:
    a) inserting a marker gene within the inverted repeats of a transposable element of claim 1 or 6 to form a modified marker gene having the structure IR-marker-IR;
    b) inserting the modified marker gene into a DNA target;
    c) selecting for expression of the modified marker; and
    d) isolating DNA upstream of said modified marker gene in said DNA target which comprises an activation sequence.

19. A method for inactivating a gene in a host cell wherein said gene encodes a gene product, the method comprising:
    a) transforming a host cell with a genetic element to create a transformed host cell, wherein the genetic element comprises DNA for the gene and a transposable element of claim 1 or 6 inserted within the DNA; and
    b) selecting for the transformed host cells deficient in the gene product.

20. A method for activating a desired gene in a host cell, the method comprising:
    a) inserting a regulatory gene within the inverted repeats of a transposable element of claim 1 or 6 to form a modified regulatory gene having the structure IR-regulatory gene-IR;
    b) inserting the modified regulatory gene in DNA comprising the desired gene to form a DNA construct containing the modified regulatory gene upstream of said desired gene;
    c) transforming the host cell with the DNA construct; and
    d) selecting for transformants expressing said desired gene.

21. A method of isolating activation sequences comprising:
    a) inserting a marker gene within the inverted repeats of a transposable element of claim 14, 15 or 16 to form a modified marker gene having the structure IR-marker-IR;
    b) inserting the modified marker gene into a DNA target;
    c) selecting for expression of the modified marker; and
    d) isolating DNA upstream of said modified marker gene in said DNA target which comprises an activation sequence.

22. A method for inactivating a gene in a host cell wherein said gene encodes a gene product, the method comprising:
   a) transforming a host cell with a genetic element to create a transformed host cell, wherein the genetic element comprises DNA for the gene and a transposable element of claim 14, 15 or 16 inserted within the DNA; and
   b) selecting for the transformed host cells deficient in the gene product.

23. A method for activating a desired gene in a host cell, the method comprising:
   a) inserting a regulatory gene within the inverted repeats of a transposable element of claim 14, 15 or 16 to form a modified regulatory gene having the structure IR-regulatory gene-IR;
   b) inserting the modified regulatory gene in DNA comprising the desired gene to form a DNA construct containing the modified regulatory gene upstream of said desired gene;
   c) transforming the host cell with the DNA construct; and
   d) selecting for transformants expressing said desired gene.

* * * * *